(12) United States Patent
Olsen et al.

(10) Patent No.: US 7,323,449 B2
(45) Date of Patent: Jan. 29, 2008

(54) THIONUCLEOSIDE DERIVATIVES AS INHIBITORS OF RNA-DEPENDENT RNA VIRAL POLYMERASE

(75) Inventors: David B. Olsen, Lansdale, PA (US); Balkrishen Bhat, Carlsbad, CA (US); Phillip Dan Cook, Fallbrook, CA (US)

(73) Assignees: Merck & Co., Inc., Rahway, NJ (US); Isis Pharmaceuticals, Inc., Carlsbad, CA (US)

( * ) Notice: Subject to any disclaimer, the term of this patent is extended or adjusted under 35 U.S.C. 154(b) by 156 days.

(21) Appl. No.: 10/520,925

(22) PCT Filed: Jul. 18, 2003

(86) PCT No.: PCT/US03/22556

§ 371 (c)(1),
(2), (4) Date: Sep. 26, 2005

(87) PCT Pub. No.: WO2004/009020

PCT Pub. Date: Jan. 29, 2004

(65) Prior Publication Data

US 2006/0122154 A1 Jun. 8, 2006

Related U.S. Application Data

(60) Provisional application No. 60/398,237, filed on Jul. 24, 2002.

(51) Int. Cl.
*C07D 487/04* (2006.01)
*A61K 31/52* (2006.01)
*A61K 31/675* (2006.01)
*C07F 9/6561* (2006.01)
*A61P 31/14* (2006.01)

(52) U.S. Cl. .................... 514/43; 514/244; 514/280; 514/81; 514/265.1; 514/52; 536/26.7; 536/27.2

(58) Field of Classification Search .............. 514/43, 514/52, 81, 265.1; 536/26.7, 27.2; 544/244, 544/280
See application file for complete search history.

(56) References Cited

U.S. PATENT DOCUMENTS

| 6,777,395 B2 | 8/2004 | Bhat et al. |
| 6,812,219 B2 | 11/2004 | LaColla et al. |
| 2003/0050229 A1 | 3/2003 | Sommadossi et al. |
| 2003/0060400 A1 | 3/2003 | LaColla et al. |
| 2004/0063658 A1 | 4/2004 | Roberts et al. |
| 2004/0072788 A1 | 4/2004 | Bhat et al. |
| 2004/0097461 A1 | 5/2004 | Sommadossi et al. |
| 2004/0147464 A1 | 7/2004 | Roberts et al. |
| 2004/0259934 A1 | 12/2004 | Olsen et al. |

FOREIGN PATENT DOCUMENTS

| WO | WO 9401117 A1 * | 1/1994 |
| WO | WO01/90121 | 11/2001 |
| WO | WO01/92282 | 12/2001 |
| WO | WO02/32920 | 4/2002 |
| WO | WO02/057287 | 7/2002 |
| WO | WO02/057425 | 7/2002 |
| WO | WO03/051899 | 6/2003 |
| WO | WO03/062255 | 7/2003 |
| WO | WO03/062256 | 7/2003 |
| WO | WO03/068244 A1 | 8/2003 |
| WO | WO03/093290 | 11/2003 |
| WO | WO03/105770 A2 | 12/2003 |
| WO | WO2004/000858 A2 | 12/2003 |
| WO | WO2004/002422 | 1/2004 |
| WO | WO2004/002999 | 1/2004 |
| WO | WO2004/007512 A2 | 1/2004 |
| WO | WO2004/009020 A2 | 1/2004 |
| WO | WO2004/028481 | 4/2004 |
| WO | WO2004/046331 | 6/2004 |
| WO | WO2004/065398 | 8/2004 |
| WO | WO2004/072090 A1 | 8/2004 |

OTHER PUBLICATIONS

M. Bobek, R. L. Whistler, and A. Bloch J. Med. Chem.; 1972; 15(2) pp. 168-171.*
Anne B. Eldrup et al., "Structure-Activity Relationship of Heterobase-Modified 2'-C-Methyl Ribonucleosides as Inhibitors of Hepatitis C Virus RNA Replication", J. Med.Chem., vol. 47, pp. 5284-5297 (2004).
Anne B. Eldrup et al., "Structure-Activity Relationship of Purine Ribonucleosides for Inhibition of Hepatitis C Virus RNA-Dependent RNA Polymerase", J. Med.Chem., vol. 47, pp. 2283-2295 (2004).
David B. Olsen et al., "A 7-Deaza-Adenosine Analog is a Potent and Selective Inhibitor of Hepatitis C Virus Replication with Excellent Pharmacokinetic Properties", Antimicrobial Agents and Chemotherapy, vol. 48, No. 10, pp. 3944-3953 (2004).

(Continued)

*Primary Examiner*—Mark L. Berch
(74) *Attorney, Agent, or Firm*—Kenneth R. Walton; Philippe L. Durette; Sheldon O. Heber

(57) ABSTRACT

The present invention provides thionucleoside compounds and certain derivatives thereof which are inhibitors of RNA-dependent RNA viral polymerase. These compounds are inhibitors of RNA-dependent RNA viral replication and are useful for the treatment of RNA-dependent RNA viral infection. They are particularly useful as inhibitors of hepatitis C virus (HCV) NS5B polymerase, as inhibitors of HCV replication, and/or for the treatment of hepatitis C infection. The invention also describes pharmaceutical compositions containing such thionucleoside compounds alone or in combination with other agents active against RNA-dependent RNA viral infection, in particular HCV infection. Also disclosed are methods of inhibiting RNA-dependent RNA polymerase, inhibiting RNA-dependent RNA viral replication, and/or treating RNA-dependent RNA viral infection with the thionucleoside compounds of the present invention.

15 Claims, No Drawings

OTHER PUBLICATIONS

Per Hoffmann et. al., "Recent Patents on Experimental Therapy for Hepatitis C Virus Infection", Expert Opin. Ther. Patents, vol. 13(11), pp. 1707-1723, (2003).

Volker Brass et al., "Recent Developments in Target Identification against Hepatitis C Virus", Expert Opin. Ther. Targets, vol. 8(4), pp. 295-307, (2004).

Murai, Y. et al. "A Synthesis and an X-Ray Analysis of 2'-C-, 3'-C-, and 5'-C-Methylsangivamycins", Heterocycles, 1992, vol. 33, pp. 391-404.

Iimori, T. et al. "A study on conformationally restricted sangivamycins and their inhibitory abilities of protien kinases", Oxford University Press, 1992, pp. 169-170.

* cited by examiner

THIONUCLEOSIDE DERIVATIVES AS INHIBITORS OF RNA-DEPENDENT RNA VIRAL POLYMERASE

CROSS REFERENCE TO RELATED APPLICATIONS

This application is the National Stage of International Application No. PCT/US03/22556 filed 18 Jul. 2003, which claims the benefit under 35 U.S.C. 119(e) of U.S. Provisional Application No. 60/398,237, filed 24 Jul. 2002.

FIELD OF THE INVENTION

The present invention is concerned with thionucleoside compounds and certain derivatives thereof, their synthesis, and their use as inhibitors of RNA-dependent RNA viral polymerase. The compounds of the present invention are inhibitors of RNA-dependent RNA viral replication and are useful for the treatment of RNA-dependent RNA viral infection. They are particularly useful as inhibitors of hepatitis C virus (HCV) NS5B polymerase, as inhibitors of HCV replication, and for the treatment of hepatitis C infection.

BACKGROUND OF THE INVENTION

Hepatitis C virus (HCV) infection is a major health problem that leads to chronic liver disease, such as cirrhosis and hepatocellular carcinoma, in a substantial number of infected individuals, estimated to be 2-15% of the world's population. There are an estimated 4.5 million infected people in the United States alone, according to the U.S. Center for Disease Control. According to the World Health Organization, there are more than 200 million infected individuals worldwide, with at least 3 to 4 million people being infected each year. Once infected, about 20% of people clear the virus, but the rest harbor HCV the rest of their lives. Ten to twenty percent of chronically infected individuals eventually develop liver-destroying cirrhosis or cancer. The viral disease is transmitted parenterally by contaminated blood and blood products, contaminated needles, or sexually and vertically from infected mothers or carrier mothers to their off-spring. Current treatments for HCV infection, which are restricted to immunotherapy with recombinant interferon-α alone or in combination with the nucleoside analog ribavirin, are of limited clinical benefit. Moreover, there is no established vaccine for HCV. Consequently, there is an urgent need for improved therapeutic agents that effectively combat chronic HCV infection. The state of the art in the treatment of HCV infection has been reviewed, and reference is made to the following publications: B. Dymock, et al., "Novel approaches to the treatment of hepatitis C virus infection," *Antiviral Chemistry & Chemotherapy*, 11: 79-96 (2000); H. Rosen, et al., "Hepatitis C virus: current understanding and prospects for future therapies," *Molecular Medicine Today*, 5: 393-399 (1999); D. Moradpour, et al., "Current and evolving therapies for hepatitis C," *European J. Gastroenterol. Hepatol.*, 11: 1189-1202 (1999); R. Bartenschlager, "Candidate Targets for Hepatitis C Virus-Specific Antiviral Therapy," *Intervirology*, 40: 378-393 (1997); G. M. Lauer and B. D. Walker, "Hepatitis C Virus Infection," *N. Engl. J. Med.*, 345: 41-52 (2001); B. W. Dymock, "Emerging therapies for hepatitis C virus infection," *Emerging Drugs*, 6: 1342 (2001); and C. Crabb, "Hard-Won Advances Spark Excitement about Hepatitis C," *Science:* 506-507 (2001); the contents of all of which are incorporated by reference herein in their entirety.

Different approaches to HCV therapy have been taken, which include the inhibition of viral serine proteinase (NS3 protease), helicase, and RNA-dependent RNA polymerase (NS5B), and the development of a vaccine.

The HCV virion is an enveloped positive-strand RNA virus with a single oligoribonucleotide genomic sequence of about 9600 bases which encodes a polyprotein of about 3,010 amino acids. The protein products of the HCV gene consist of the structural proteins C, E1, and E2, and the non-structural proteins NS2, NS3, NS4A and NS4B, and NS5A and NS5B. The nonstructural (NS) proteins are believed to provide the catalytic machinery for viral replication. The NS3 protease releases NS5B, the RNA-dependent RNA polymerase from the polyprotein chain. HCV NS5B polymerase is required for the synthesis of a double-stranded RNA from a single-stranded viral RNA that serves as a template in the replication cycle of HCV. NS5B polymerase is therefore considered to be an essential component in the HCV replication complex [see K. Ishi, et al., "Expression of Hepatitis C Virus NS5B Protein: Characterization of Its RNA Polymerase Activity and RNA Binding," *Hepatology*, 29: 1227-1235 (1999) and V. Lohmann, et al., "Biochemical and Kinetic Analyses of NS5B RNA-Dependent RNA Polymerase of the Hepatitis C Virus," *Virology*, 249: 108-118 (1998)]. Inhibition of HCV NS5B polymerase prevents formation of the double-stranded HCV RNA and therefore constitutes an attractive approach to the development of HCV-specific antiviral therapies.

It has now been found that thionucleoside compounds of the present invention and certain derivatives thereof are potent inhibitors of RNA-dependent RNA viral replication and in particular HCV replication. The 5'-triphosphate derivatives of these thionucleoside compounds are inhibitors of RNA-dependent RNA viral polymerase and in particular HCV NS5B polymerase. The instant thionucleoside compounds and derivatives thereof are useful to treat RNA-dependent RNA viral infection and in particular HCV infection.

It is therefore an object of the present invention to provide thionucleoside compounds and certain derivatives thereof which are useful as inhibitors of RNA-dependent RNA viral polymerase and in particular as inhibitors of HCV NS5B polymerase.

It is another object of the present invention to provide thionucleoside compounds and certain derivatives thereof which are useful as inhibitors of the replication of an RNA-dependent RNA virus and in particular as inhibitors of the replication of hepatitis C virus.

It is another object of the present invention to provide thionucleoside compounds and certain derivatives thereof which are useful in the treatment of RNA-dependent RNA viral infection and in particular in the treatment of HCV infection.

It is another object of the present invention to provide pharmaceutical compositions comprising the thionucleoside compounds of the present invention in association with a pharmaceutically acceptable carrier.

It is another object of the present invention to provide pharmaceutical compositions comprising the thionucleoside compounds and derivatives thereof of the present invention for use as inhibitors of RNA-dependent RNA viral polymerase and in particular as inhibitors of HCV NS5B polymerase.

It is another object of the present invention to provide pharmaceutical compositions comprising the thionucleoside compounds and derivatives thereof of the present invention for use as inhibitors of RNA-dependent RNA viral replication and in particular as inhibitors of HCV replication.

It is another object of the present invention to provide pharmaceutical compositions comprising the thionucleoside compounds and derivatives thereof of the present invention for use in the treatment of RNA-dependent RNA viral infection and in particular in the treatment of HCV infection.

It is another object of the present invention to provide pharmaceutical compositions comprising the thionucleoside compounds and derivatives thereof of the present invention in combination with other agents active against an RNA-dependent RNA virus and in particular against HCV.

It is another object of the present invention to provide methods for the inhibition of RNA-dependent RNA viral polymerase and in particular for the inhibition of HCV NS5B polymerase.

It is another object of the present invention to provide methods for the inhibition of RNA-dependent RNA viral replication and in particular for the inhibition of HCV replication.

It is another object of the present invention to provide methods for the treatment of RNA-dependent RNA viral infection and in particular for the treatment of HCV infection.

It is another object of the present invention to provide methods for the treatment of RNA-dependent RNA viral infection in combination with other agents active against RNA-dependent RNA virus and in particular for the treatment of HCV infection in combination with other agents active against HCV.

It is another object of the present invention to provide thionucleoside compounds and certain derivatives thereof and their pharmaceutical compositions for use as a medicament for the inhibition of RNA-dependent RNA viral replication and/or the treatment of RNA-dependent RNA viral infection and in particular for the inhibition of HCV replication and/or the treatment of HCV infection.

It is another object of the present invention to provide for the use of the thionucleoside compounds and certain derivatives thereof of the present invention and their pharmaceutical compositions for the manufacture of a medicament for the inhibition of RNA-dependent RNA viral replication and/or the treatment of RNA-dependent RNA viral infection and in particular for the inhibition of HCV replication and/or the treatment of HCV infection.

These and other objects will become readily apparent from the detailed description which follows.

SUMMARY OF THE INVENTION

The present invention relates to compounds of structural formula I of the indicated stereochemical configuration:

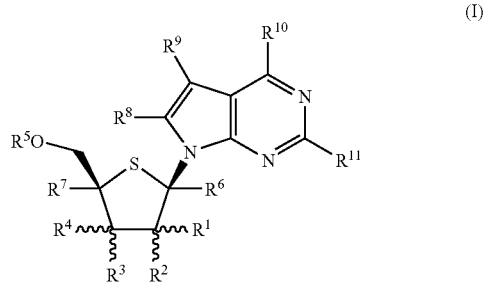

(I)

or a pharmaceutically acceptable salt thereof;

wherein $R^1$ is $C_{1-4}$ alkyl, wherein alkyl is unsubstituted or substituted with hydroxy, amino, $C_{1-4}$ alkoxy, $C_{1-4}$ alkylthio, or one to three fluorine atoms;

$R^2$ is amino, fluorine, hydroxy, mercapto, $C_{1-4}$ alkoxy, or $C_{1-10}$ alkylcarbonyloxy;

$R^3$ and $R^4$ are each independently selected from the group consisting of hydrogen, cyano, azido, halogen, hydroxy, mercapto, amino, $C_{1-4}$ alkoxy, $C_{1-10}$ alkylcarbonyloxy, $C_{2-4}$ alkenyl, $C_{2-4}$ alkynyl, and $C_{1-4}$ alkyl, wherein alkyl is unsubstituted or substituted with hydroxy, amino, $C_{1-4}$ alkoxy, $C_{1-4}$ alkylthio, or one to three fluorine atoms;

$R^5$ is hydrogen, $C_{1-10}$ alkylcarbonyl, $P_3O_9H_4$, $P_2O_6H_3$, or $P(O)R^{13}R^{14}$;

$R^6$ and $R^7$ are each independently hydrogen, methyl, hydroxymethyl, or fluoromethyl;

$R^8$ is hydrogen, $C_{1-4}$ alkyl, $C_{2-4}$ alkynyl, halogen, cyano, carboxy, $C_{1-4}$ alkyloxycarbonyl, azido, amino, $C_{1-4}$ alkylamino, di($C_{1-4}$ alkyl)amino, hydroxy, $C_{1-6}$ alkoxy, $C_{1-6}$ alkylthio, $C_{1-6}$ alkylsulfonyl, or $(C_{1-4}$ alkyl$)_{0-2}$ aminomethyl;

$R^9$ is hydrogen, cyano, nitro, $C_{1-3}$ alkyl, $NHCONH_2$, $CONR^{12}R^{12}$, $CSNR^{12}R^{12}$, $COOR^{12}$, $C(=NH)NH_2$, hydroxy, $C_{1-3}$ alkoxy, amino, $C_{1-4}$ alkylamino, di($C_{1-4}$ alkyl)amino, halogen, (1,3-oxazol-2-yl), (1,3-thiazol-2-yl), or (imidazol-2-yl); wherein alkyl is unsubstituted or substituted with one to three groups independently selected from halogen, amino, hydroxy, carboxy, and $C_{1-3}$ alkoxy;

$R^{10}$ and $R^{11}$ are each independently hydrogen, hydroxy, halogen, $C_{1-4}$ alkoxy, amino, $C_{1-4}$ alkylamino, di($C_{1-4}$ alkyl)amino, $C_{3-6}$ cycloalkylamino, di($C_{3-6}$ cycloalkyl)amino, or $C_{4-6}$ cycloheteroalkyl, unsubstituted or substituted with one to two groups independently selected from halogen, hydroxy, amino, $C_{1-4}$ alkyl, and $C_{1-4}$ alkoxy;

each $R^{12}$ is independently hydrogen or $C_{1-6}$ alkyl; and $R^{13}$ and $R^{14}$ are each independently hydroxy, $OCH_2CH_2SC(=O)C_{1-4}$ alkyl, $OCH_2O(C=O)OC_{1-4}$ alkyl, $NHCHMeCO_2Me$, $OCH(C_{1-4}$ alkyl$)O(C=O)C_{1-4}$ alkyl,

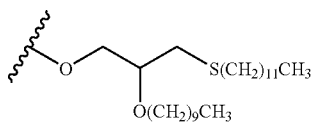

or

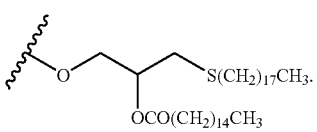

The compounds of formula I are useful as inhibitors of RNA-dependent RNA viral polymerase and in particular of HCV NS5B polymerase. They are also inhibitors of RNA-dependent RNA viral replication and in particular of HCV replication and are useful for the treatment of RNA-dependent RNA viral infection and in particular for the treatment of HCV infection.

Also encompassed within the present invention are pharmaceutical compositions containing the compounds alone or in combination with other agents active against RNA-dependent RNA virus and in particular against HCV as well as methods for the inhibition of RNA dependent RNA viral replication and for the treatment of RNA-dependent RNA viral infection.

DETAILED DESCRIPTION OF THE INVENTION

The present invention relates to compounds of structural formula I of the indicated stereochemical configuration:

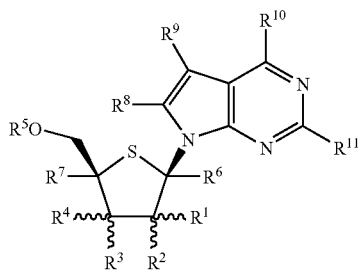

(I)

or a pharmaceutically acceptable salt thereof;
wherein $R^1$ is $C_{1-4}$ alkyl, wherein alkyl is unsubstituted or substituted with hydroxy, amino, $C_{1-4}$ alkoxy, $C_{1-4}$ alkylthio, or one to three fluorine atoms;

$R^2$ is amino, fluorine, hydroxy, mercapto, $C_{1-4}$ alkoxy, or $C_{1-10}$ alkylcarbonyloxy;

$R^3$ and $R^4$ are each independently selected from the group consisting of hydrogen, cyano, azido, halogen, hydroxy, mercapto, amino, $C_{1-4}$ alkoxy, $C_{1-10}$ alkylcarbonyloxy, $C_{2-4}$ alkenyl, $C_{2-4}$ alkynyl, and $C_{1-4}$ alkyl, wherein alkyl is unsubstituted or substituted with hydroxy, amino, $C_{1-4}$ alkoxy, $C_{1-4}$ alkylthio, or one to three fluorine atoms;

$R^5$ is hydrogen, $C_{1-10}$ alkylcarbonyl, $P_3O_9H_4$, $P_2O_6H_3$, or $P(O)R^{13}R^{14}$;

$R^6$ and $R^7$ are each independently hydrogen, methyl, hydroxymethyl, or fluoromethyl;

$R^8$ is hydrogen, $C_{1-4}$ alkyl, $C_{2-4}$ alkynyl, halogen, cyano, carboxy, $C_{1-4}$ alkyloxycarbonyl, azido, amino, $C_{1-4}$ alkylamino, di($C_{1-4}$ alkyl)amino, hydroxy, $C_{1-6}$ alkoxy, $C_{1-6}$ alkylthio, $C_{1-6}$ alkylsulfonyl, or ($C_{1-4}$ alkyl)$_{0-2}$ aminomethyl;

$R^9$ is hydrogen, cyano, nitro, $C_{1-3}$ alkyl, NHCONH$_2$, CONR$^{12}$R$^{12}$, CSNR$^{12}$R$^{12}$, COOR$^{12}$, C(=NH)NH$_2$, hydroxy, $C_{1-3}$ alkoxy, amino, $C_{1-4}$ alkylamino, di($C_{1-4}$ alkyl)amino, halogen, (1,3-oxazol-2-yl), (1,3-thiazol-2-yl), or (imidazol-2-yl); wherein alkyl is unsubstituted or substituted with one to three groups independently selected from halogen, amino, hydroxy, carboxy, and $C_{1-3}$ alkoxy;

$R^{10}$ and $R^{11}$ are each independently hydrogen, hydroxy, halogen, $C_{1-4}$ alkoxy, amino, $C_{1-4}$ alkylamino, di($C_{1-4}$ alkyl)amino, $C_{3-6}$ cycloalkylamino, di($C_{3-6}$ cycloalkyl)amino, or $C_{4-6}$ cycloheteroalkyl, unsubstituted or substituted with one to two groups independently selected from halogen, hydroxy, amino, $C_{1-4}$ alkyl, and $C_{1-4}$ alkoxy;

each $R^{12}$ is independently hydrogen or $C_{1-6}$ alkyl; and $R^{13}$ and $R^{14}$ are each independently hydroxy, OCH$_2$CH$_2$SC(=O)C$_{1-4}$ alkyl, OCH$_2$O(C=O)OC$_{1-4}$ alkyl, NHCHMeCO$_2$Me, OCH(C$_{1-4}$ alkyl)O(C=O)C$_{1-4}$ alkyl,

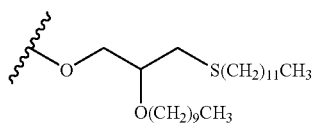

or

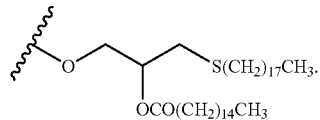

The compounds of formula I are useful as inhibitors of RNA-dependent RNA viral polymerase. They are also inhibitors of RNA-dependent RNA viral replication and are useful for the treatment of RNA-dependent RNA viral infection.

In one embodiment of the compounds of structural formula I are the compounds of structural formula II:

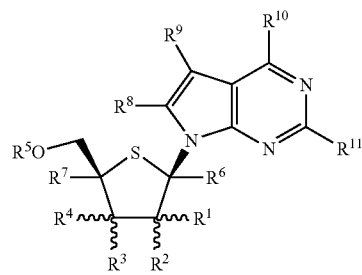

(II)

or a pharmaceutically acceptable salt thereof;
wherein
$R^1$ is $C_{1-3}$ alkyl, wherein alkyl is unsubstituted or substituted with hydroxy, amino, $C_{1-3}$ alkoxy, $C_{1-3}$ alkylthio, or one to three fluorine atoms;

$R^2$ is hydroxy, fluoro, $C_{1-3}$ alkoxy, or $C_{1-8}$ alkylcarbonyloxy;

$R^3$ is hydrogen, halogen, hydroxy, amino, $C_{1-3}$ alkoxy, or $C_{1-8}$ alkylcarbonyloxy;

$R^5$ is hydrogen, $C_{1-8}$ alkylcarbonyl, $P_3O_9H_4$, $P_2O_6H_3$, or PO$_3$H$_2$;

$R^8$ is hydrogen, amino, or $C_{1-4}$ alkylamino;

$R^9$ is hydrogen, cyano, methyl, halogen, or CONH$_2$; and $R^{10}$ and $R^{11}$ are each independently hydrogen, halogen, hydroxy, amino, $C_{1-4}$ alkylamino, di($C_{1-4}$ alkyl)amino, or $C_{3-6}$ cycloalkylamino.

In a second embodiment of the compounds of structural formula I are the compounds of structural formula II wherein:

$R^1$ is methyl, fluoromethyl, hydroxymethyl, difluoromethyl, trifluoromethyl, or aminomethyl;

$R^2$ is hydroxy, fluoro, or methoxy;

$R^3$ is hydrogen, fluoro, hydroxy, amino, or methoxy;

$R^5$ is hydrogen or $P_3O_9H_4$;

$R^8$ is hydrogen or amino;

$R^9$ is hydrogen, cyano, methyl, halogen, or CONH$_2$; and $R^{10}$ and $R^{11}$ are each independently hydrogen, fluoro, hydroxy, or amino.

Illustrative but nonlimiting examples of compounds of the present invention of structural formula I which are useful as inhibitors of RNA-dependent RNA viral polymerase are the following:

4-amino-7-(2-C-methyl-4-thio-β-D-ribofuranosyl)-7H-pyrrolo[2,3-d]pyrimidine and 2-amino-7-(2-C-methyl-4-thio-β-D-ribofuranosyl)7H-pyrrolo[2,3-d]pyrimidin-4(3H)-one;

and the corresponding 5'-triphosphates;
or a pharmaceutically acceptable salt thereof.

In one embodiment of the present invention, the thionucleoside compounds of the present invention are useful as inhibitors of positive-sense single-stranded RNA-dependent RNA viral polymerase, inhibitors of positive-sense single-stranded RNA-dependent RNA viral replication, and/or for the treatment of positive-sense single-stranded RNA-dependent RNA viral infection. In a class of this embodiment, the positive-sense single-stranded RNA-dependent RNA virus is a Flaviviridae virus or a Picornaviridae virus. In a subclass of this class, the Picornaviridae virus is a rhinovirus, a poliovirus, or a hepatitis A virus. In a second subclass of this class, the Flaviviridae virus is selected from the group consisting of hepatitis C virus, yellow fever virus, dengue virus, West Nile virus, Japanese encephalitis virus, Banzi virus, and bovine viral diarrhea virus (BVDV). In a subclass of this subclass, the Flaviviridae virus is hepatitis C virus.

Another aspect of the present invention is concerned with a method for inhibiting RNA-dependent RNA viral polymerase, a method for inhibiting RNA-dependent RNA viral replication, and/or a method for treating RNA-dependent RNA viral infection in a mammal in need thereof comprising administering to the mammal a therapeutically effective amount of a compound of structural formula I.

In one embodiment of this aspect of the present invention, the RNA-dependent RNA viral polymerase is a positive-sense single-stranded RNA-dependent RNA viral polymerase. In a class of this embodiment, the positive-sense single-stranded RNA-dependent RNA viral polymerase is a Flaviviridae viral polymerase or a Picornaviridae viral polymerase. In a subclass of this class, the Picornaviridae viral polymerase is rhinovirus polymerase, poliovirus polymerase, or hepatitis A virus polymerase. In a second subclass of this class, the Flaviviridae viral polymerase is selected from the group consisting of hepatitis C virus polymerase, yellow fever virus polymerase, dengue virus polymerase, West Nile virus polymerase, Japanese encephalitis virus polymerase, Banzi virus polymerase, and bovine viral diarrhea virus (BVDV) polymerase. In a subclass of this subclass, the Flaviviridae viral polymerase is hepatitis C virus polymerase.

In a second embodiment of this aspect of the present invention, the RNA-dependent RNA viral replication is a positive-sense single-stranded RNA-dependent RNA viral replication. In a class of this embodiment, the positive-sense single-stranded RNA-dependent RNA viral replication is Flaviviridae viral replication or Picornaviridae viral replication. In a subclass of this class, the Picornaviridae viral replication is rhinovirus replication, poliovirus replication, or hepatitis A virus replication. In a second subclass of this class, the Flaviviridae viral replication is selected from the group consisting of hepatitis C virus replication, yellow fever virus replication, dengue virus replication, West Nile virus replication, Japanese encephalitis virus replication, Banzi virus replication, and bovine viral diarrhea virus replication. In a subclass of this subclass, the Flaviviridae viral replication is hepatitis C virus replication.

In a third embodiment of this aspect of the present invention, the RNA-dependent RNA viral infection is a positive-sense single-stranded RNA-dependent viral infection. In a class of this embodiment, the positive-sense single-stranded RNA-dependent RNA viral infection is Flaviviridae viral infection or Picornaviridae viral infection. In a subclass of this class, the Picornaviridae viral infection is rhinovirus infection, poliovirus infection, or hepatitis A virus infection. In a second subclass of this class, the Flaviviridae viral infection is selected from the group consisting of hepatitis C virus infection, yellow fever virus infection, dengue virus infection, West Nile virus infection, Japanese encephalitis virus infection, Banzi virus infection, and bovine viral diarrhea virus infection. In a subclass of this subclass, the Flaviviridae viral infection is hepatitis C virus infection.

Throughout the instant application, the following terms have the indicated meanings:

The alkyl groups specified above are intended to include those alkyl groups of the designated length in either a straight or branched configuration. Exemplary of such alkyl groups are methyl, ethyl, propyl, isopropyl, butyl, sec-butyl, tertiary butyl, pentyl, isopentyl, hexyl, isohexyl, and the like.

The term "alkenyl" shall mean straight or branched chain alkenes of two to six total carbon atoms, or any number within this range (e.g., ethenyl, propenyl, butenyl, pentenyl, etc.).

The term "alkynyl" shall mean straight or branched chain alkenes of two to six total carbon atoms, or any number within this range (e.g., ethynyl, propynyl, butynyl, pentynyl, etc.).

The term "cycloalkyl" shall mean cyclic rings of alkanes of three to eight total carbon atoms, or any number within this range (i.e., cyclopropyl, cyclobutyl, cyclopentyl, cyclohexyl, cycloheptyl, or cyclooctyl).

The term "cycloheteroalkyl" is intended to include non-aromatic heterocycles containing one or two heteroatoms selected from nitrogen, oxygen and sulfur. Examples of 4-6-membered cycloheteroalkyl include azetidinyl, pyrrolidinyl, piperidinyl, morpholinyl, thiamorpholinyl, imidazolidinyl, tetrahydrofuranyl, tetrahydropyranyl, tetrahydrothiophenyl, piperazinyl, and the like.

The term "alkoxy" refers to straight or branched chain alkoxides of the number of carbon atoms specified (e.g., $C_{1-4}$ alkoxy), or any number within this range [i.e., methoxy (MeO—), ethoxy, isopropoxy, etc.].

The term "alkylthio" refers to straight or branched chain alkylsulfides of the number of carbon atoms specified (e.g., $C_{1-4}$ alkylthio), or any number within this range [i.e., methylthio (MeS—), ethylthio, isopropylthio, etc.].

The term "alkylamino" refers to straight or branched alkylamines of the number of carbon atoms specified (e.g., $C_{1-4}$ alkylamino), or any number within this range [i.e., methylamino, ethylamino, isopropylamino, t-butylamino, etc.].

The term "alkylsulfonyl" refers to straight or branched chain alkylsulfones of the number of carbon atoms specified (e.g., $C_{1-6}$ alkylsulfonyl), or any number within this range [i.e., methylsulfonyl ($MeSO_2$—), ethylsulfonyl, isopropylsulfonyl, etc.].

The term "alkyloxycarbonyl" refers to straight or branched chain esters of a carboxylic acid derivative of the present invention of the number of carbon atoms specified (e.g., $C_{1-4}$ alkyloxycarbonyl), or any number within this range [i.e., methyloxycarbonyl (MeOCO—), ethyloxycarbonyl, or butyloxycarbonyl].

The term "aryl" includes both phenyl, naphthyl, and pyridyl. The aryl group is optionally substituted with one to three groups independently selected from $C_{1-4}$ alkyl, halogen, cyano, nitro, trifluoromethyl, $C_{1-4}$ alkoxy, and $C_{1-4}$ alkylthio.

The term "halogen" is intended to include the halogen atoms fluorine, chlorine, bromine and iodine.

The term "substituted" shall be deemed to include multiple degrees of substitution by a named substituent. Where multiple substituent moieties are disclosed or claimed, the substituted compound can be independently substituted by one or more of the disclosed or claimed substituent moieties, singly or plurally.

The term "5'-triphosphate" refers to a triphosphoric acid ester derivative of the 5'-hydroxyl group of a thionucleoside compound of the present invention having the following general structural formula III:

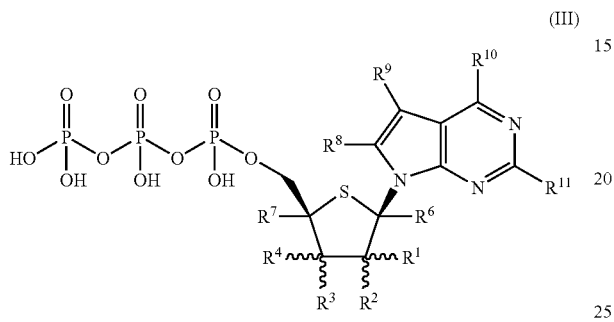

(III)

wherein $R^1$—$R^{11}$ are as defined above. The compounds of the present invention are also intended to include pharmaceutically acceptable salts of the triphosphate ester as well as pharmaceutically acceptable salts of 5'-monophosphate and 5'-diphosphate ester derivatives of the structural formulae IV and V, respectively,

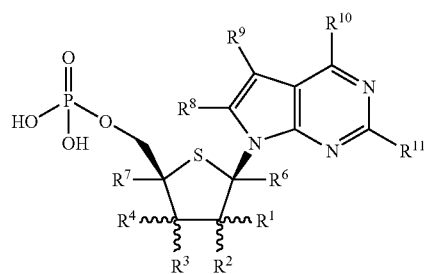

(IV)

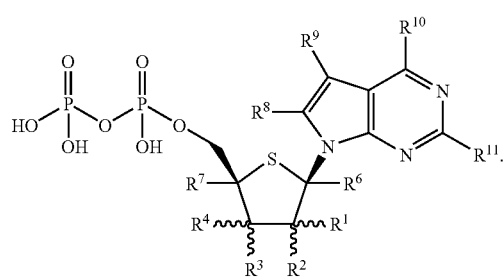

(V)

The term "5'-(S-acyl-2-thioethyl)phosphate" or "SATE" refers to a mono- or di-ester derivative of a 5'-monophosphate thionucleoside derivative of the present invention of structural formulae VI and VII, respectively, as well as pharmaceutically acceptable salts of the mono-ester,

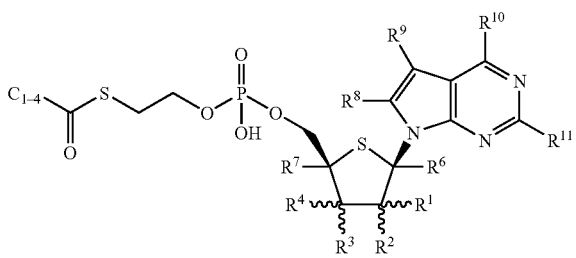

VI

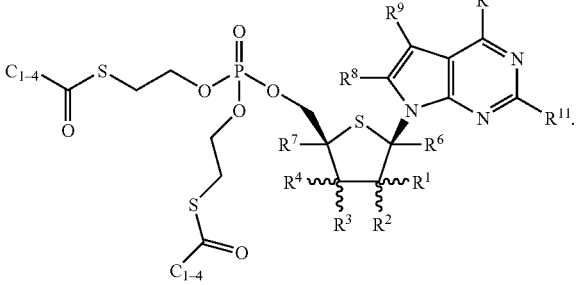

VII

The term "composition", as in "pharmaceutical composition," is intended to encompass a product comprising the active ingredient(s) and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

The terms "administration of" and "administering a" compound should be understood to mean providing a compound of the invention or a prodrug of a compound of the invention to the individual in need.

Another aspect of the present invention is concerned with a method of inhibiting HCV NS5B polymerase, inhibiting HCV replication, or treating HCV infection with a compound of the present invention in combination with one or more agents useful for treating HCV infection. Such agents active against HCV include, but are not limited to, ribavirin, levovirin, viramidine, thymosin alpha-1, interferon-β, interferon-α, pegylated interferon-α (peginterferon-α), a combination of interferon-α and ribavirin, a combination of peginterferon-α and ribavirin, a combination of interferon-α and levovirin, and a combination of peginterferon-α and levovirin. Interferon-α includes, but is not limited to, recombinant interferon-α2a (such as Roferon interferon available from Hoffmann-LaRoche, Nutley, N.J.), pegylated interferon-α2a (Pegasys™), interferon-α2b (such as Intron-A interferon available from Schering Corp., Kenilworth, N.J.), pegylated interferon-α2b (PegIntron™), a recombinant consensus interferon (such as interferon alphacon-1), and a purified interferon-α product. Amgen's recombinant consensus interferon has the brand name Infergen®. Levovirin is the L-enantiomer of ribavirin which has shown immunomodulatory activity similar to ribavirin. Viramidine represents an analog of ribavirin disclosed in WO 01/60379 (assigned to ICN Pharmaceuticals). In accordance with this method of the present invention, the individual components of the combination can be administered separately at different times during the course of therapy or concurrently in divided or single combination forms. The instant invention is therefore to be understood as embracing all such regimes of simultaneous or alternating treatment, and the term "administering" is to be interpreted accordingly. It will be understood that the scope of combinations of the compounds of this invention with other agents useful for treating HCV infection includes in principle any combination with any pharmaceutical composition for treating HCV infection. When a compound of the present invention or a pharmaceutically acceptable salt thereof is, used in combination with a second therapeutic agent active against HCV, the dose of each compound may be either the same as or different from the dose when the compound is used alone.

For the treatment of HCV infection, the compounds of the present invention may also be administered in combination with an agent that is an inhibitor of HCV NS3 serine protease. HCV NS3 serine protease is an essential viral enzyme and has been described to be an excellent target for inhibition of HCV replication. Both substrate and non-substrate based inhibitors of HCV NS3 protease inhibitors are disclosed in WO 98/22496, WO 98/46630, WO 99/07733, WO 99/07734, WO 99/38888, WO 99/50230, WO 99/64442, WO 00/09543, WO 00/59929, GB-2337262, WO 02/48116, WO 02/48172, and U.S. Pat. No. 6,323,180. HCV NS3 protease as a target for the development of inhibitors of HCV replication and for the treatment of HCV infection is discussed in B. W. Dymock, "Emerging therapies for hepatitis C virus infection," *Emerging Drugs*, 6: 13-42 (2001).

Ribavirin, levovirin, and viramidine may exert their anti-HCV effects by modulating intracellular pools of guanine nucleotides via inhibition of the intracellular enzyme inosine monophosphate dehydrogenase (IMPDH). IMPDH is the rate-limiting enzyme on the biosynthetic route in de novo guanine nucleotide biosynthesis. Ribavirin is readily phosphorylated intracellularly and the monophosphate derivative is an inhibitor of IMPDH. Thus, inhibition of IMPDH represents another useful target for the discovery of inhibitors of HCV replication. Therefore, the compounds of the present invention may also be administered in combination with an inhibitor of IMPDH, such as VX-497, which is disclosed in WO 97/41211 and WO 01/00622 (assigned to Vertex); another IMPDH inhibitor, such as that disclosed in WO 00/25780 (assigned to Bristol-Myers Squibb); or mycophenolate mofetil [see A. C. Allison and E. M. Eugui, *Agents Action*, 44 (Suppl.): 165 (1993)].

For the treatment of HCV infection, the compounds of the present invention may also be administered in combination with the antiviral agent amantadine (1-aminoadamantane) [for a comprehensive description of this agent, see J. Kirschbaum, *Anal. Profiles Drug Subs.* 12: 1-36 (1983)].

The compounds of the present invention may also be combined for the treatment of HCV infection with antiviral 2'-C-branched ribonucleosides disclosed in R. E. Harry-O'kuru, et al., *J. Org. Chem.*, 62: 1754-1759 (1997); M. S. Wolfe, et al., *Tetrahedron Lett.*, 36: 7611-7614 (1995); U.S. Pat. No. 3,480,613 (Nov. 25, 1969); International Publication Number WO 01/90121 (29 Nov. 2001); International Publication Number WO 01/92282 (6 Dec. 2001); and International Publication Number WO 02/32920 (25 Apr. 2002); the contents of each of which are incorporated by reference in their entirety. Such 2'-C-branched ribonucleosides include, but are not limited to, 2'-C-methyl-cytidine, 2'-C-methyl-uridine, 2'-C-methyl-adenosine, 2'-C-methyl-guanosine, and 9-(2-C-methyl-β-D-ribofuranosyl)-2,6-diaminopurine.

The compounds of the present invention may also be combined for the treatment of HCV infection with other nucleosides having anti-HCV properties, such as those disclosed in WO 02/51425 (4 Jul. 2002), assigned to Mitsubishi Pharma Corp.; WO 01/79246, WO 02/32920, and WO 02/48165 (20 Jun. 2002), assigned to Pharmasset, Ltd.; WO 01/68663 (20 Sep. 2001), assigned to ICN Pharmaceuticals; WO 99/43691 (2 Sep. 1999); WO 02/18404 (7 Mar. 2002), assigned to Hoffmann-LaRoche; and U.S. 2002/0019363 (14 Feb. 2002).

The compounds of the present invention may also be combined for the treatment of HCV infection with non-nucleoside inhibitors of HCV polymerase such as those disclosed in WO 0177091 (18 Oct. 2001), assigned to Tularik, Inc.; WO 01/47883 (5 Jul. 2001), assigned to Japan Tobacco, Inc.; WO 02/04425 (17 Jan. 2002), assigned to Boehringer Ingelheim; WO 02/06246 (24 Jan. 2002), assigned to Istituto di Ricerche di Biologia Moleculare P. Angeletti S. P. A.; and WO 02/20497 (3 Mar. 2002).

By "pharmaceutically acceptable" is meant that the carrier, diluent, or excipient must be compatible with the other ingredients of the formulation and not deleterious to the recipient thereof.

Also included within the present invention are pharmaceutical compositions comprising the thionucleoside compounds and derivatives thereof of the present invention in association with a pharmaceutically acceptable carrier. Another example of the invention is a pharmaceutical composition made by combining any of the compounds described above and a pharmaceutically acceptable carrier. Another illustration of the invention is a process for making a pharmaceutical composition comprising combining any of the compounds described above and a pharmaceutically acceptable carrier.

Also included within the present invention are pharmaceutical compositions useful for inhibiting RNA-dependent RNA viral polymerase in particular HCV NS5B polymerase comprising an effective amount of a compound of the present invention and a pharmaceutically acceptable carrier. Pharmaceutical compositions useful for treating RNA-dependent RNA viral infection in particular HCV infection are also encompassed by the present invention as well as a method of inhibiting RNA-dependent RNA viral polymerase in particular HCV NS5B polymerase and a method of treating RNA-dependent viral replication and in particular HCV replication. Additionally, the present invention is directed to a pharmaceutical composition comprising a therapeutically effective amount of a compound of the present invention in combination with a therapeutically effective amount of another agent active against RNA-dependent RNA virus and in particular against HCV. Agents active against HCV include, but are not limited to, ribavirin, levovirin, viramidine, thymosin alpha-1, an inhibitor of HCV NS3 serine protease, interferon-α, pegylated interferon-α (peginterferon-α), a combination of interferon-α and ribavirin, a combination of peginterferon-a and ribavirin, a combination of interferon-α and levovirin, and a combination of peginterferon-α and levovirin. Interferon-α includes, but is not limited to, recombinant interferon-α2a (such as Roferon interferon available from Hoffmann-LaRoche, Nutley, N.J.), interferon-α2b (such as Intron-A interferon available from Schering Corp., Kenilworth, N.J.), a consensus interferon, and a purified interferon-α product. For a discussion of ribavirin and its activity against HCV, see J. O. Saunders and S. A. Raybuck, "Inosine Monophosphate Dehydrogenase: Consideration of Structure, Kinetics, and Therapeutic Potential," *Ann. Rep. Med. Chem.*, 35: 201-210 (2000).

Another aspect of the present invention provides for the use of the thionucleoside compounds and derivatives thereof and their pharmaceutical compositions for the manufacture of a medicament for the inhibition of RNA-dependent RNA viral replication, in particular HCV replication, and/or the treatment of RNA-dependent RNA viral infection, in particular HCV infection. Yet a further aspect of the present invention provides for the thionucleoside compounds and derivatives thereof and their pharmaceutical compositions for use as a medicament for the inhibition of RNA-dependent RNA viral replication, in particular HCV replication, and/or for the treatment of RNA-dependent RNA viral infection, in particular HCV infection.

The pharmaceutical compositions of the present invention comprise a compound of structural formula I as an active ingredient or a pharmaceutically acceptable salt thereof, and may also contain a pharmaceutically acceptable carrier and optionally other therapeutic ingredients.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of structural formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of structural formula I may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous reparation of sterile injectable solutions or dispersions. In all cases, the form must be sterile and must be fluid to the extent that easy syringability exists. It must:be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of structural formula I are administered orally.

For oral administration to humans, the dosage range is 0.01 to 1000 mg/kg body weight in divided doses. In one embodiment the dosage range is 0.1 to 100 mg/kg body weight in divided doses. In another embodiment the dosage range is 0.5 to 20 mg/kg body weight in divided doses. For oral administration, the compositions are preferably provided in the form of tablets or capsules containing 1.0 to 1000 milligrams of the active ingredient, particularly, 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated.

The effective dosage of active ingredient employed may vary depending on the particular compound employed, the mode of administration, the condition being treated and the severity of the condition being treated. Such dosage may be ascertained readily by a person skilled in the art. This dosage regimen may be adjusted to provide the optimal therapeutic response.

The compounds of the present invention contain one or more asymmetric centers and can thus occur as racemates and racemic mixtures, single enantiomers, diastereomeric mixtures and individual diastereomers. The present invention is meant to comprehend thionucleoside compounds having the β-D stereochemical configuration for the five-membered furanose ring as depicted in the structural formula below, that is, thionucleoside compounds in which the substituents at C-1 and C-4 of the five-membered furanose ring have the β-stereochemical configuration ("up" orientation as denoted by a bold line).

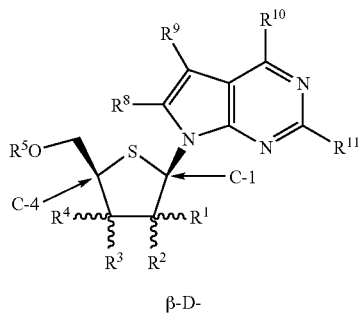

β-D-

Some of the compounds described herein contain olefinic double bonds, and unless specified otherwise, are meant to include both E and Z geometric isomers.

Some of the compounds described herein may exist as tautomers such as keto-enol tautomers. The individual tautomers as well as mixtures thereof are encompassed with compounds of structural formula I. An example of keto-enol; tautomers which are intended to be encompassed within the compounds of the present invention is illustrated below:

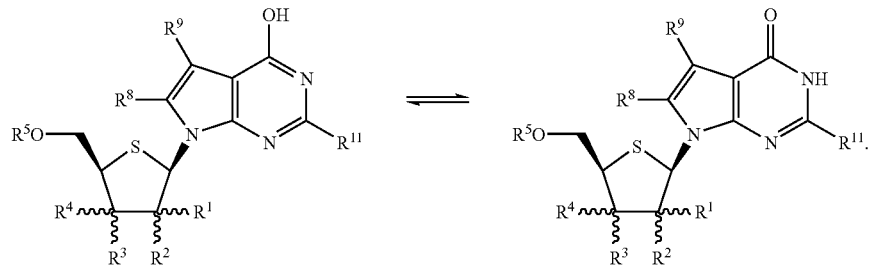

Compounds of structural formula I may be separated into their individual diastereoisomers by, for example, fractional crystallization from a suitable solvent, for example methanol or ethyl acetate or a mixture thereof, or via chiral chromatography using an optically active stationary phase.

Alternatively, any stereoisomer of a compound of the structural formula I may be obtained by stereospecific synthesis using optically pure starting materials or reagents of known configuration.

The stereochemistry of the substituents at the C-2 and C-3 positions of the furanose ring of the compounds of the present invention of structural formula I is denoted by squiggly lines which signifies that substituents $R^1$, $R^2$, $R^3$ and $R^4$ can have either the I (substituent "down") or θ (substituent "up") configuration independently of one another. Notation of stereochemistry by a bold line as at C-1 and C-4 of the furanose ring signifies that the substituent has the β-configuration (substituent "up").

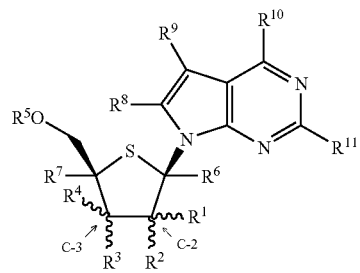

(I)

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucaamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N- dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamnine, isopropylamine, lysine, methylglucamine, morpholine, piperazine, piperidine, polyamine resins, procaine, purines, theobromine, triethylamine, trimethylamine, tripropylamine, tromethamine, and the like.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as acetate or maleate, can be employed. Included are those esters and acyl groups known in the art for modifying the solubility or hydrolysis characteristics for use as sustained-release or prodrug formulations.

Preparation of the Thionucleoside Compounds and Derivatives of the Invention

The thionucleoside compounds and derivatives thereof of the present invention can be prepared following synthetic methodologies well-established in the practice of nucleoside and nucleotide chemistry. Reference is made to the following text for a description of synthetic methods used in the preparation of the compounds of the present invention: "Chemistry of Nucleosides and Nucleotides," L. B. Townsend, ed., Vols. 1-3, Plenum Press, 1988, which is incorporated by reference herein in its entirety. In particular reference is made to the following article and references cited therein for methods of preparation of thionucleosides wherein the ring oxygen is replaced with a sulfur: L. Bellon, et al., "4'-Thio-RNA: a novel class of sugar-modified β-RNA," ACS Symposium Series (1994), 580 (Carbohydrate Modifications in Antisense Research), pages 68-79.

The examples below provide citations to literature publications which contain details for the preparation of intermediates employed in the preparation of final compounds of the present invention. The thionucleoside compounds of the present invention were prepared according to procedures detailed in the following examples. The examples are not intended to be limitations on the scope of the instant invention in any way, and they should not be so construed. Those skilled in the art of nucleoside and nucleotide synthesis will readily appreciate that known variations of the conditions and processes of the following preparative procedures can be used to prepare these and other compounds of the present invention. All temperatures are degrees Celsius unless otherwise noted.

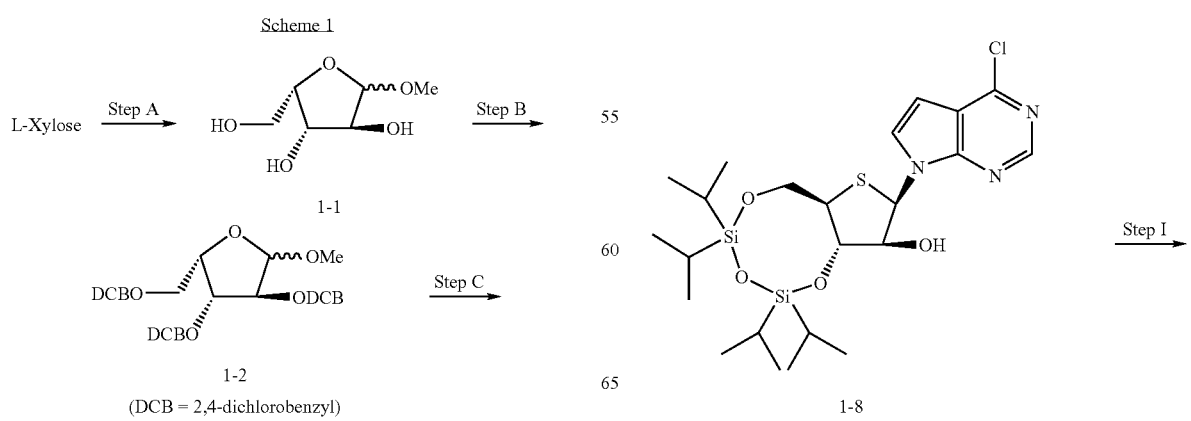

(DCB = 2,4-dichlorobenzyl)

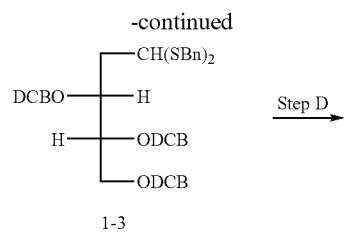

1-3

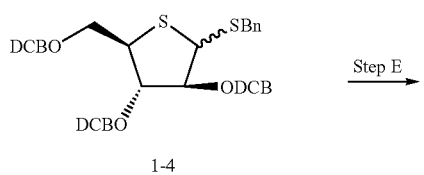

1-4

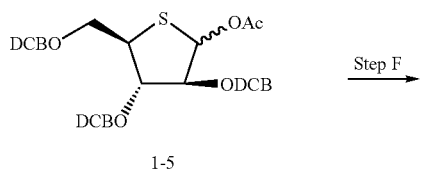

1-5

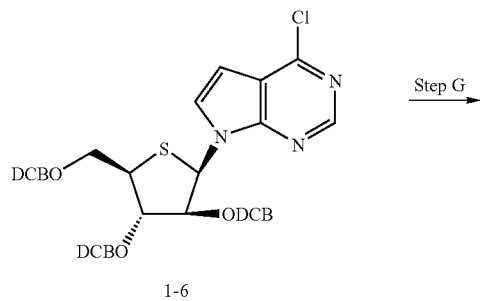

1-6

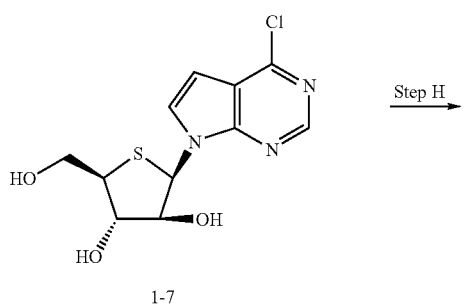

1-7

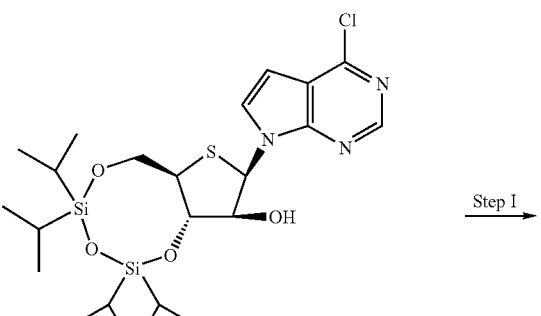

1-8

-continued

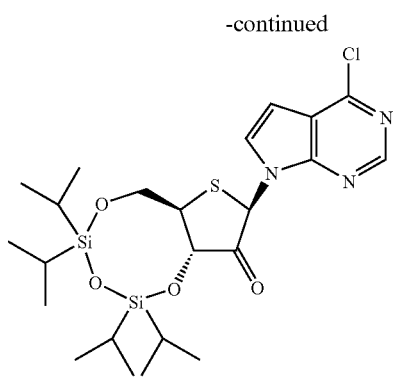

1-9

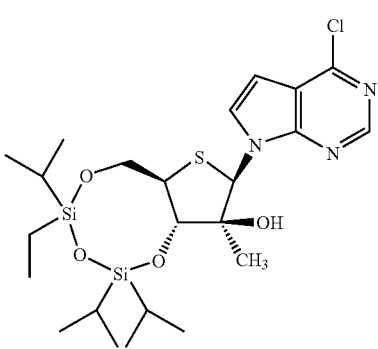

1-10a

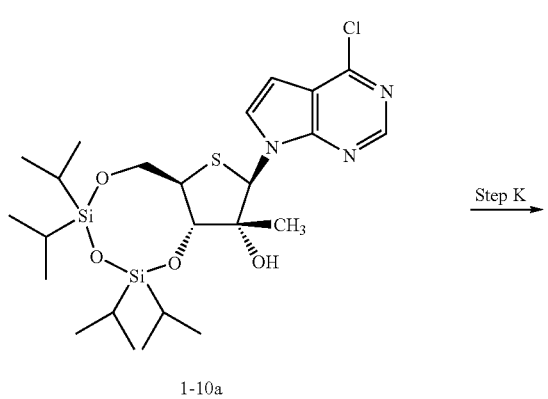

1-10a

+

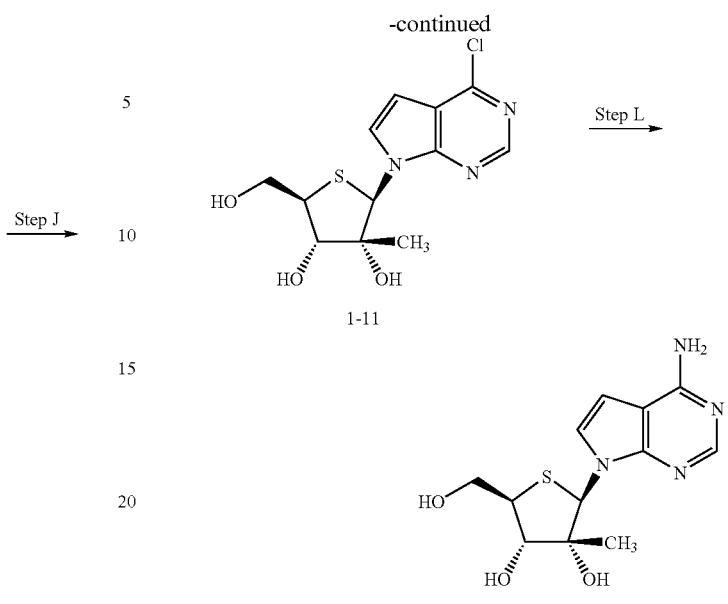

1-11

1-12

EXAMPLE 1

4-Amino-7-(2-C-methyl-4-thio-β-D-ribofuranosyl)-7H-pyrrolo[2,3-d]pyrimidine (1-12)

Step A: Methyl L-xylofuranoside (1-1)

This compound is prepared according to the procedure described in *J. Med. Chem.* 41: 3865 (1998). L-Xylose is stirred in 0.5N HCl in anhydrous MeOH for 5-10 h at room temperature. The reaction mixture is neutralized with Amberlite IRA-400 OH or Dowex—X200 anion exchange resin. The resin is removed by filtration. The combined filtrate and washings are concentrated to an oil which is subjected to column chromatography on silica gel using a mixture of $CH_2Cl_2$ and MeOH as the eluent to afford compound 1-1 as an α/β anomeric mixture.

Step B: 2,3,5-Tri-O-(2,4-dichlorobenzyl)-1-O-methyl-L-xylofuranose (1-2)

Compound 1-1 from Step A is dissolved in anhydrous TBF and the solution is cooled in an ice bath. To the cold solution is added sodium hydride (60% dispersion in mineral oil) and the reaction mixture is stirred for 35 to 45 min under an argon atmosphere. To this mixture is added 2,4-dichlorobenzyl chloride slowly over 20 min. The reaction mixture is stirred for 72 h, then cooled in an ice bath. MeOH is added slowly to decompose excess NaH. The mixture is concentrated under reduced pressure and the residue is taken up in ethyl acetate and washed several times with water. The organic layer is dried over anhydrous $Na_2SO_4$, filtered, and evaporated. The residue is purified by silica gel chromatography using a mixture of hexane and ethyl acetate as the eluent. The appropriate fractions are combined and evaporated to afford compound 1-2.

Step C: 2,3,5-Tri-O-(2,4dichlorobenzyl)-L-xylose dibenzyl dithioacetal (1-3)

This compound is prepared by a similar procedure as that described for the preparation of 2,3,5-tri-O-benzyl-L-xylose dibenzyl dithioacetal [*J. Med. Chem.* 41: 3865 (1998)]. To a solution of compound 1-2 from Step B in $CH_2Cl_2$ is added benzyl mercaptan and tin tetrachloride. The reaction mixture is stirred at room temperature for 15 h. The reaction mixture is then neutralized with 5% aqueous $NaHCO_3$ solution. The organic layer is separated and the aqueous layer is extracted with $CH_2Cl_2$. The combined layers are concentrated, and the residue is purified on a silica gel column using a mixture of cyclohexane and ethyl acetate as the eluent. Removal of the solvent affords the title compound 1-3.

Step D: Benzyl 2,3,5-tri-O-(2,4-dichlorobenzyl)-1,4-dithio-D-arabinofuranoside (1-4)

This compound is prepared under similar experimental conditions as those described for the corresponding perbenzylated derivative [*J. Med. Chem.* 41: 3865 (1998)]. To a solution of compound 1-3 from Step C in a 2:1 mixture of anhydrous toluene/acetonitrile is added triphenylphosphine, imidazole and iodine. The reaction mixture is stirred at 90° C. for 24 h. The reaction is concentrated to dryness and the product is purified by silica gel chromatography eluting with a mixture of cyclohexane and ethyl acetate to furnish compound 1-4.

Step E: 2,3,5-Tri-O-(2,4-dichlorobenzyl)-1-O-acetyl-4-thio-D-arabinofuranose (1-5)

To a suspension of mercuric acetate in acetic acid is added compound 1-4 from Step D and the resulting reaction mixture is stirred at room temperature for 2-3 h. The mixture is then diluted with $CH_2Cl_2$, washed with water, saturated aqueous sodium bicarbonate and 5% KCN solution. The organic layer is dried over anhydrous sodium sulfate, filtered, and evaporated. The residue is purified on a silica gel column using a mixture of cyclohexane and ethyl acetate as eluent. The appropriate fractions are combined and concentrated to give the title compound 1-5.

Step F: 4-Chloro-7-[2,3,5-tri-O-(2,4-dichlorobenzyl)-4-thio-β-D-arabinofuranosyl]-7H-pyrrolo[2,3-d]pyrimidine (1-6)

To a solution of the compound 1-5 from Step E (1 eq) in anhydrous dichloromethane at 0° C. is added HBr (5 eq) dropwise. The resulting solution is stirred at 0° C. for 1 h and then at room temperature for 3 h, evaporated and co-evaporated with anhydrous toluene. The oily residue is dissolved in anhydrous acetonitrile, and the solution is added to a mixture of the sodium salt of 4-chloro-1H-pyrrolo[2,3-d]pyrimidine [for preparation, see *J. Chem. Soc.,* 131 (1960)] in acetonitrile [generated in situ from 4-chloro-1H-pyrrolo[2,3-d]pyrimidine (3 eq) in anhydrous acetonitrile and NaH (60% in mineral oil, 3 eq) with stirring at room temperature for 4 h]. The reaction mixture is stirred at room temperature for 24 h, and then evaporated to dryness. The residue is suspended in water and extracted with EtOAc. The combined extracts are washed with brine, dried over $Na_2SO_4$, filtered and evaporated. The mixture of α/β anomers is resolved either by silica gel chromatography or chiral chromatography using ethyl acetate/hexane as the eluent. Appropriate fractions are combined and evaporated in vacuo to give the desired β-D-arabinofuranosyl isomer 1-6.

Step G: 4-Chloro-7-(4-thio-β-D-arabinofuranosyl)-7H-pyrrolo-[2,3-d]pyrimidine (1-7)

To a solution of compound 1-6 from Step F (1 eq) in dichloromethane at −78° C. is added boron trichloride (1M in dichloromethane, 10 eq) dropwise. The mixture is stirred at −78° C. then at −30° C. to −20° C. The reaction is quenched by addition of methanol/dichloromethane (1:1) and the resulting mixture stirred at −15° C., then neutralized with aqueous ammonia at 0° C. and stirred at room temperature. The solid is filtered and washed with $CH_2Cl_2$/MeOH (1/1). The combined filtrate and washings are evaporated, and the residue is purified by flash chromatography over silica gel using $CH_2Cl_2$ and $CH_2Cl_2$:MeOH gradient as the eluent to furnish the title compound 1-7.

Step H: 4-Chloro-7-(3,5-O-tetraisopropyldisiloxanediyl-4-thio-β-D-arabinofuranosyl)-7H-pyrrolo-[2,3-d]pyrimidine (1-8)

To dried compound 1-8 from Step G (1 eq) in anhydrous pyridine is added 1,3-dichloro-1,1,3,3-tetraisopropyldisiloxane (1.2 eq) and the mixture is stirred several hours. Pyridine is removed by evaporation and the residue is partitioned between EtOAc and $H_2O$. The organic phase is washed with cold 1N HCl, water, saturated aqueous sodium hydrogencarbonate and finally with brine. The organic layer is dried over anhydrous $Na_2SO_4$, filtered and evaporated. The resulting product is purified on a silica gel column using a mixture of $CH_2Cl_2$/MeOH as the eluent. The solvent is removed under reduced pressure to give the title compound 1-8.

Step I: 4Chloro-7-(3,5-O-tetraisopropyldisiloxanediyl-4-thio-β-D-erythro-pentofuran-2-ulosyl)-7H-pyrrolo-[2,3-d]pyrimidine (1-9)

A mixture of compound 1-8 from step H (1 eq), 1,3-dicyclohexylcarbodiimide (3 eq) and phosphoric acid (0.5 eq) in DMSO is stirred at room temperature overnight. The residue is purified by column chromatography over silica gel using $CH_2Cl_2$:MeOH as eluent to furnish the title compound 1-9.

Step J: 4-Chloro-7-(3,5-O-tetraisopropyldisiloxanediyl-2-C-methyl-4-thio-β-D-ribofuranosyl)-7H-pyrrolo-[2,3-d]pyrimidine (1-10a) & 4-chloro-7-(3,5-O-tetraisopropyldisiloxanediyl-2-C-methyl-4-thio-β-D-arabinofuranosyl)-7H-pyrrolo-[2,3-d]pyrimidine (1-10b)

To a cooled solution (−10° C.) of compound 1-9 from step I (1 eq) in anhydrous toluene under argon is added methylmagnesium bromide (3M soln. in ether, 2 eq) and the mixture is stirred for several hours. To this mixture is added an additional amount of $CH_3MgBr$ (1 eq) and stirring is continued overnight at room temperature. The mixture is then cooled to 0° C. and poured onto ice water and extracted with ethyl acetate. The organic layer is washed with water and dried over anhydrous $Na_2SO_4$, filtered, and evaporated. The crude product is purified by column chromatography over silica gel using a mixture of acetone and dichloromethane to furnish the β-methyl (ribo) isomer (1-10a) and the α-methyl (arabino) isomer (1-10b).

Step K: 4-Chloro-7-(2-C-methyl-4-thio-β-D-ribofuranosyl)-7H-pyrrolo-[2,3-d]pyrimidine (1-11)

To a solution of 1-10a in anhydrous TBF is added triethylamine (5 eq) and triethylamine trihydrofluoride (10 eq) and reaction mixture is stirred at room temperature overnight. It is then evaporated and coevaporated with toluene and purified by column chromatography over silica gel using a mixture of MeOH in dichloromethane as eluent to furnish the title compound 1-11.

Step L: 4-Amino-7-(2-C-methyl-4-thio-β-D-ribofuranosyl)-7H-pyrrolo[2,3-d]pyrimidine (1-12)

To the compound from Step K is added methanolic ammonia (saturated at 0° C.). The mixture is heated in a stainless steel autoclave at 85° C. for 14 h, then cooled and evaporated in vacuo. The crude mixture is purified on a silica gel column using a mixture of $CH_2Cl_2$/MeOH as eluent to give the title compound 1-12.

Scheme 2
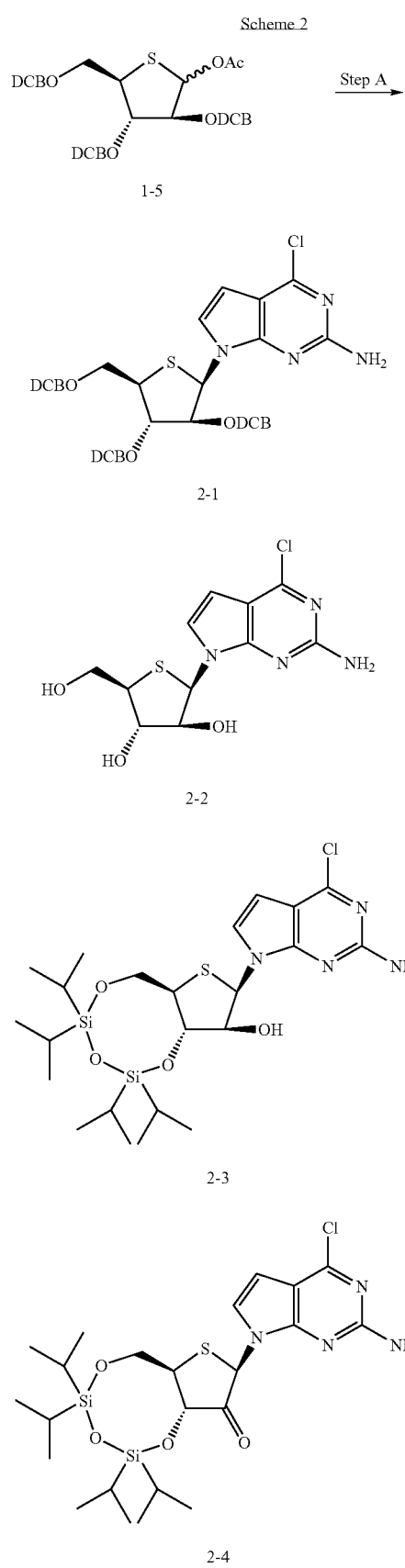
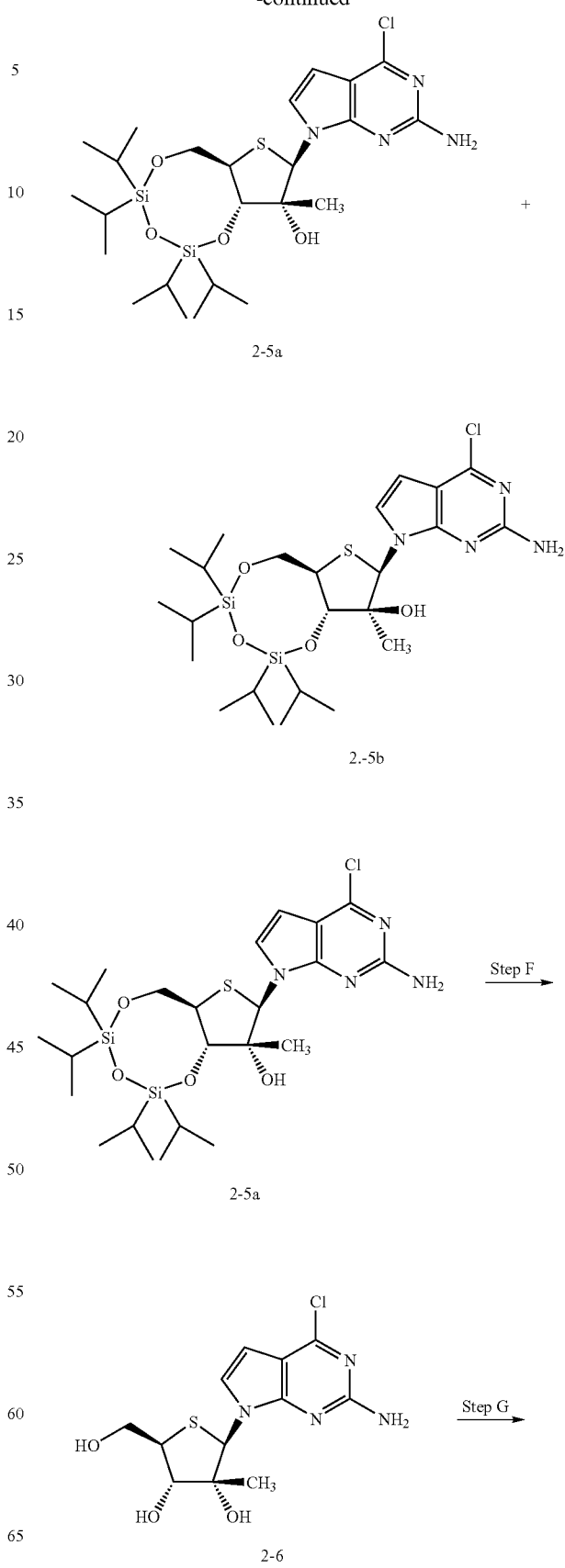

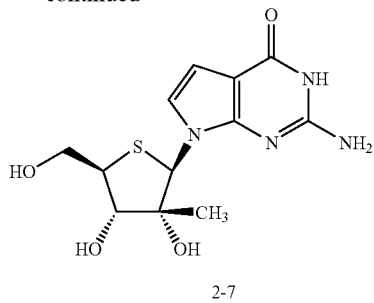

2-7

EXAMPLE 2

2-Amino-7-(2-C-methyl-4-thio-β-D-ribofuranosyl)-7H-pyrrolo[2,3-d]pyrimidin-4(3H)-one (2-7)

Step A: 2-Amino4-chloro-7-[2,3,5-tri-O-(2,4dichlorobenzyl)-4-thio-β-D-arabinofuranosyl]-7H-pyrrolo[2,3-d]pyrimidine (2-1)

To a solution of the compound 1-5 from Step E of Example 1 (1 eq.) in anhydrous dichloromethane at 0° C. is added HBr (5 eq) dropwise. The resulting solution is stirred at 0° C. for 1 h and then at room temperature for 3 h, evaporated in vacuo and co-evaporated with anhydrous toluene. The oily residue is dissolved in anhydrous acetonitrile and added to a solution of the sodium salt of 2-amino-4-chloro-1H-pyrrolo[2,3-d]pyrimidine [for preparation of similar compound, see J. Chem. Soc., 131 (1960)] in acetonitrile [generated in situ from 2-amino4-chloro-1H-pyrrolo[2,3-d]pyrimidine (3 eq) in anhydrous acetonitrile and NaH (60% in mineral oil, 3 eq), with stirring at room temperature for 4 h]. The reaction mixture is stirred at room temperature for 24 h, and then evaporated to dryness. The residue is suspended in water and extracted with EtOAc. The combined extracts are washed with brine, dried over Na₂SO₄, filtered and evaporated. The mixture of α/β anomers is resolved either by silica gel chromatography or chiral chromatography using ethyl acetate/hexane as the eluent. Appropriate fractions are combined and evaporated in vacuo to give the desired β-D-arabinofuranosyl isomer 2-1.

Step B: 2-Amino4chloro-7-(4-thio-β-D-arabinofuranosyl)-7H-pyrrolo[2,3-d]pyrimidine (2-2)

To a solution of the compound from Step A in anhydrous CH₂Cl₂ at −78° C. is added a solution of 1.0 M BCl₃ in CH₂Cl₂ during 45 min. The mixture is stirred at −78° C. for 3 h and at −20° C. for 2.5 h. MeOH—CH₂Cl₂ (1:1) is added to the mixture, which is then stirred at −20° C. for 0.5 h and neutralized with conc. aqueous NH₃ at 0° C. The mixture is then stirred at room temperature for 10 min. and filtered. The solid is washed with MeOH—CH₂Cl₂ (1:1) and the combined filtrate and washings evaporated. The residue is purified on a silica gel column with a mixture of CH₂Cl₂/MeOH as eluent to give the title compound 2-2.

Step C: 2-Amino-7-[3,5-O-(tetraisopropyldisiloxanediyl)-4-thio-β-D-arabinofuranosyl]-4chloro-7H-pyrrolo[2,3-d]pyrimidine (2-3)

The compound from Step B (1 eq) and imidazole (2 eq) are dissolved in DMF. 1,3-Dichloro-1,1,3,3-tetraisopropyldisiloxane (1.1 eq) is added to the solution. The reaction mixture is stirred at room temperature for 3 h and then evaporated. The residue is partitioned between CH₂Cl₂ and water. The layers are separated. The organic layer is dried (Na₂SO₄) and evaporated. The residue is purified on a silica gel column with a mixture of hexanes/EtOAc as eluent to give the title compound 2-3.

Step D: 2-Amino-4-chloro-7-(3,5-O-tetraisopropyldisiloxanediyl4-thio-β-D-erythro-pentofuran-2-ulosyl)-7H-pyrrolo-[2,3-d]pyrimidine (2-4)

A mixture of compound 2-3 obtained from Step C (1 eq), 1,3-dicyclohexylcarbodiimide (3 eq) and phosphoric acid (0.5 eq) in DMSO is stirred at room temperature overnight. The residue-is purified by column chromatography over silica gel using CH₂Cl₂:MeOH as eluent to furnish the title compound 2-4.

Step E: 2-Amino4-chloro-7-(3,5-O-tetraisopropyldisiloxanediyl-2-C-methyl-4-thio-β-D-ribofuranosyl)-7H-pyrrolo-[2,3-d]pyrimidine (2-5a) & 2-amino-4chloro-7-(3,5-O-tetraisopropyldisiloxanediyl-2-C-methyl-4-thio-β-D-arabinofuranosyl)-7H-pyrrolo-[2,3-d]pyrimidine (2-5b)

To a cooled solution (−10° C.) of compound 2-4 from Step D (1 eq) in anhydrous toluene under argon is added methylmagnesium bromide (3M soln. in ether, 2 eq.) and the mixture is stirred for several hours. To this mixture is added an additional amount of CH₃MgBr (1 eq) and stirring is continued overnight at room temperature. The mixture is then cooled to 0° C. and poured onto ice water and extracted with ethyl acetate. The organic layer is washed with water and dried over anhydrous Na₂SO₄, filtered, and evaporated. The crude product is purified by column chromatography over silica gel using a mixture of acetone and dichloromethane to furnish the β-methyl (ribo) isomer (2-5a) and the α-methyl (arabino) isomer (2-5b).

Step F: 2-Amino-4-chloro-7-(2-C-methyl-4-thio-β-D-ribofuranosyl)-7H-pyrrolo-[2,3-d]pyrimidine (2-6)

To a solution of 2-5a in anhydrous THF is added triethylamine (5 eq) and triethylamine trihydrofluoride (10 eq) and reaction mixture is stirred at room temperature overnight. It is concentrated in vacuo and coevaporated with toluene and purified by column chromatography over silica gel using a mixture of MeOH in dichloromethane as eluent to furnish desired compound 2-6.

Step G: 2-Amino-7-(2-C-methyl-4-thio-β-D-ribofuranosyl)-7H-pyrrolo[2,3-d]pyrimidin-4(3H)-one (2-7)

A mixture of the compound from Step F in 2N aqueous NaOH is stirred at reflux temperature for 1.5 h. The solution is cooled in an ice-bath, neutralized with 2 N aqueous HCl and evaporated to dryness. The residue is suspended in MeOH, mixed with silica gel and evaporated. The solid residue is placed onto a silica gel column (packed in a solvent system of CH₂Cl₂/MeOH). The compound is eluted with a solvent system of CH₂Cl₂/MeOH. The fractions containing the product are collected and evaporated to dryness to yield the title compound 2-7.

BIOLOGICAL ASSAYS

The assays employed to measure the inhibition of HCV NS5B polymerase and HCV replication are described below.

The effectiveness of the compounds of the present invention as inhibitors of HCV NS5B RNA-dependent RNA polymerase (RdRp) was measured in the following assay.

A. Assay for Inhibition of HCV NS5B Polymerase:

This assay was used to measure the ability of the thionucleoside derivatives of the present invention to inhibit the enzymatic activity of the RNA-dependent RNA polymerase (NS5B) of the hepatitis C virus (HCV) on a heteromeric RNA template.

Procedure:
Assay Buffer Conditions: (50 μL-total/reaction)
20 mM Tris, pH 7.5
50 μM EDTA
5 mM DTT
2 mM $MgCl_2$
80 mM KCl
0.4 U/μL RNAsin (Promega, stock is 40 units/μL)
0.75 μg t500 (a 500-nt RNA made using T7 runoff transcription with a sequence from the NS2/3 region of the hepatitis C genome)
1.6 μg purified hepatitis C NS5B (form with 21 amino acids C-terminally truncated)
1 μM A,C,U,GTP (Nucleoside triphosphate mix)
[alpha-$^{32}$P]-GTP or [alpha-$^{33}$P]-GTP The compounds were tested at various concentrations up to 100 μM final concentration.

An appropriate volume of reaction buffer was made including enzyme and template t500. Thionucleoside derivatives of the present invention were pipetted into the wells of a 96-well plate. A mixture of nucleoside triphosphates (NTP's), including the radiolabeled GTP, was made and pipetted into the wells of a 96-well plate. The reaction was initiated by addition of the enzyme-template reaction solution and allowed to proceed at room temperature for 1-2 h.

The reaction was quenched by addition of 20 μL 0.5M EDTA, pH 8.0. Blank reactions in which the quench solution was added to the NTPs prior to the addition of the reaction buffer were included.

50 μL of the quenched reaction were spotted onto DE81 filter disks (Whatman) and allowed to dry for 30 min. The filters were washed with 0.3 M ammonium formate, pH 8 (150 mL/wash until the cpm in 1 mL wash is less than 100, usually 6 washes). The filters were counted in 5-mL scintillation fluid in a scintillation counter.

The percentage of inhibition was calculated according to the following equation: % Inhibition=[1−(cpm in test reaction−cpm in blank)/(cpm in control reaction−cpm in blank)]×100.

Representative compounds tested in the HCV NS5B polymerase assay exhibited $IC_{50}$'s less than 100 micromolar.

B. Assay for Inhibition of HCV RNA Replication:

The compounds of the present invention were also evaluated for their ability to affect the replication of Hepatitis C Virus RNA in cultured hepatoma (HuH-7) cells containing a subgenomic HCV Replicon. The details of the assay are described below. This Replicon assay is a modification of that described in V. Lohmann, F. Korner, J-O. Koch, U. Herian, L. Theilmann, and R. Bartenschlager, "Replication of a Sub-genomic Hepatitis C Virus RNAs in a Hepatoma Cell Line," *Science* 285:110 (1999).

Protocol:

The assay was an in situ Ribonuclease protection, Scintillation Proximity based-plate assay (SPA). 10,000-40,000 cells were plated in 100-200 μL of media containing 0.8 mg/mL G418 in 96-well cytostar plates (Amersham). Compounds were added to cells at various concentrations up to 100 μM in 1% DMSO at time 0 to 18 h and then cultured for 24-96 h. Cells were fixed (20 min, 10% formalin), permeabilized (20 min, 0.25% Triton X-100/PBS) and hybridized (overnight, 50° C.) with a single-stranded $^{33}$P RNA probe complementary to the (+) strand NS5B (or other genes) contained in the RNA viral genome. Cells were washed, treated with RNAse, washed, heated to 65° C. and counted in a Top-Count. Inhibition of replication was read as a decrease in counts per minute (cpm).

Human HuH-7 hepatoma cells, which were selected to contain a subgenomic replicon, carry a cytoplasmic RNA consisting of an HCV 5' non-translated region (NTR), a neomycin selectable marker, an EMCV IRES (internal ribosome entry site), and HCV non-structural proteins NS3 through NS5B, followed by the 3' NTR.

Representative compounds tested in the replication assay exhibited $EC_{50}$'s less than 100 micromolar.

The thionucleoside derivatives of the present invention were also evaluated for cellular toxicity and anti-viral specificity in the counterscreens described below.

C. Counterscreens:

The ability of the thionucleoside derivatives of the present invention to inhibit human DNA polymerases was measured in the following assays.

a. Inhibition of Human DNA Polymerases Alpha and Beta:

Reaction Conditions:
50 μL reaction volume

Reaction Buffer Components:
20 mM Tris-HCl, pH 7.5
200 μg/mL bovine serum albumin
100 mM KCl
2 mM β-mercaptoethanol
10 mM $MgCl_2$
1.6 μM dA, dG, dC, dTTP
α-$^{33}$P-dATp Enzyme and Template:
0.05 mg/mL gapped fish sperm DNA template
0.01 U/μL DNA polymerase α or β

Preparation of Gapped Fish Sperm DNA Template:
Add 5 μL 1M $MgCl_2$ to 500 μL activated fish sperm DNA (USB 70076);
Warm to 37° C. and add 30 μL of 65 U/μL of exonuclease III (GibcoBRL 18013-011);
Incubate 5 min at 37° C.;
Terminate reaction by heating to 65° C. for 10 min;
Load 50-100 μL aliquots onto Bio-spin 6 chromatography columns (Bio-Rad 732-6002) equilibrated with 20 mM Tris-HCl, pH 7.5;
Elute by centrifugation at 1,000×g for 4 min;
Pool eluate and measure absorbance at 260 nm to determine concentration.

The DNA template was diluted into an appropriate volume of 20 mM Tris-HCl, pH 7.5 and the enzyme was diluted into an appropriate volume of 20 mM Tris-HCl, containing 2 mM β-mercaptoethanol, and 100 mM KCl. Template and enzyme were pipetted into microcentrifuge tubes or a 96 well plate. Blank reactions excluding enzyme and control reactions excluding test compound were also prepared using enzyme dilution buffer and test compound solvent, respectively. The reaction was initiated with reaction buffer with components as listed above. The reaction wars incubated for 1 hour at 37° C. The reaction was quenched by the addition of 20 μL 0.5M EDTA. 50 μL of the quenched reaction was spotted onto Whatman DE81 filter disks and air dried. The filter disks were repeatedly washed with 150 mL 0.3M ammonium formate, pH 8 until 1 mL of wash is <100 cpm. The disks were washed twice with 150 mL absolute ethanol and once with 150 mL anhydrous ether, dried and counted in 5 mL scintillation fluid.

The percentage of inhibition was calculated according to the following equation: % inhibition=[1−(cpm in test reaction−cpm in blank)/(cpm in control reaction−cpm in blank)]×100.

b. Inhibition of Human DNA Polymerase Gamma:

The potential for inhibition of human DNA polymerase gamma was measured in reactions that included 0.5 ng/μL enzyme; 10 μM DATP, dGTP, dCTP, and TTP; 2 μCi/reaction [α-$^{33}$P]-dATP, and 0.4 μg/μL activated fish sperm DNA purchased from US Biochemical) in a buffer containing 20 mM Tris pH8, 2 mM β-mercaptoethanol, 50 mM KCl, 10 mM MgCl$_2$, and 0.1 μg/μL BSA. Reactions were allowed to proceed for 1 h at 37° C. and were quenched by addition of 0.5 M EDTA to a final concentration of 142 mM. Product formation was quantified by anion exchange filter binding and scintillation counting. Compounds were tested at up to 50 μM.

The percentage of inhibition was calculated according to the following equation: % inhibition=[1−(cpm in test reaction−cpm in blank)/(cpm in control reaction−cpm in blank)]×100.

The ability of the thionucleoside derivatives of the present invention to inhibit HIV infectivity and HIV spread was measured in the following assays.

c. HIV Infectivity Assay

Assays were performed with a variant of HeLa Magi cells expressing both CXCR4 and CCR5 selected for low background β-galactosidase (β-gal) expression. Cells were infected for 48 h, and β-gal production from the integrated HIV-1 LTR promoter was quantified with a chemiluminescent substrate (Galactolight Plus, Tropix, Bedford, Mass.). Inhibitors were titrated (in duplicate) in twofold serial dilutions starting at 100 μM; percent inhibition at each concentration was calculated in relation to the control infection.

d. Inhibition of HIV Spread

The ability of the compounds of the present invention to inhibit the spread of the human immunedeficiency virus (HIV) was measured by the method described in U.S. Pat. No. 5,413,999 (May 9, 1995), and J. P. Vacca, et al., *Proc. Natl. Acad. Sci.*, 91: 4096-4100 (1994), which are incorporated by reference herein in their entirety.

The thionucleoside derivatives of the present invention were also screened for cytotoxicity against cultured hepatoma (HuH-7) cells containing a subgenomic HCV Replicon in an MTS cell-based assay as described in the assay below. The HuH-7 cell line is described in H. Nakabayashi, et al., *Cancer Res.*, 42: 3858 (1982).

e. Cytotoxicity Assay:

Cell cultures were prepared in appropriate media at concentrations of approximately 1.5×10$^5$ cells/mL for suspension cultures in 3 day incubations and 5.0×10$^4$ cells/mL for adherent cultures in 3 day incubations. 99 μL of cell culture was transferred to wells of a 96-well tissue culture treated plate, and 1 μL of 100-times final concentration of the test compound in DMSO was added. The plates were incubated at 37° C. and 5% CO$_2$ for a specified period of time. After the incubation period, 20 μL of CellTiter 96 Aqueous One Solution Cell Proliferation Assay reagent (MWS) (Promega) was added to each well and the plates were incubated at 37° C. and 5% CO$_2$ for an additional period of time up to 3 h. The plates were agitated to mix well and absorbance at 490 nm was read using a plate reader. A standard curve of suspension culture cells was prepared with known cell numbers just prior to the addition of MTS reagent. Metabolically active cells reduce MTS to formazan. Formazan absorbs at 490 nm. The absorbance at 490 nm in the presence of compound was compared to absorbance in cells without any compound added. *Reference:* Cory, A. H. et al., "Use of an aqueous soluble tetrazolium/formazan assay for cell growth assays in culture," *Cancer Commun.* 3: 207 (1991).

The following assays were employed to measure the activity of the compounds of the present invention against other RNA-dependent RNA viruses:

a. Determination of In Vitro Antiviral Activity of Compounds Against Rhinovirus (Cytopathic Effect Inhibition Assay):

Assay conditions are described in the article by Sidewall and Huffman, "Use of disposable microtissue culture plates for antiviral and interferon induction studies," *Appl. Microbiol.* 22: 797-801 (1971).

Viruses:

Rhinovirus type 2 (RV-2), strain HGP, was used with KB cells and media (0.1% NaHCO$_3$, no antibiotics) as stated in the Sidwell and Huffman reference. The virus, obtained from the ATCC, was from a throat swab of an adult male with a mild acute febrile upper respiratory illness.

Rhinovirus type 9 (RV-9), strain 211, and rhinovirus type 14 (RV-14), strain Tow, were also obtained from the American Type Culture Collection (ATCC) in Rockville, Md. RV-9 was from human throat washings and RV-14 was from a throat swab of a young adult with upper respiratory illness. Both of these viruses were used with HeLa Ohio-1 cells (Dr. Fred Hayden, Univ. of VA) which were human cervical epitheloid carcinoma cells. MEM (Eagle's minimum essential medium) with 5% Fetal Bovine serum (FBS) and 0.1% NaHCO$_3$ was used as the growth medium.

Antiviral test medium for all three virus types was MEM with 5% FBS, 0.1% NaHCO$_3$, 50 μg gentamicin/mL, and 10 mM MgCl$_2$.

2000 μg/mL was the highest concentration used to assay the compounds of the present invention. Virus was added to the assay plate approximately 5 rain after the test compound. Proper controls were also run. Assay plates were incubated with humidified air and 5% CO$_2$ at 37° C. Cytotoxicity was monitored in the control cells microscopically for morphologic changes. Regression analysis of the virus CPE data and the toxicity control data gave the ED50 (50% effective dose) and CC50 (50% cytotoxic concentration). The selectivity index (SI) was calculated by the formula: SI=CC50÷ED50.

b. Determination of In Vitro Antiviral Activity of Compounds Against Dengue, Banzi, and Yellow Fever (CPE Inhibition Assay Assay details are provided in the Sidewall and Huffman reference above.

Viruses:

Dengue virus type 2, New Guinea strain, was obtained from the Center for Disease Control. Two lines of African green monkey kidney cells were used to culture the virus (Vero) and to perform antiviral testing (MA-104). Both Yellow fever virus, 17D strain, prepared from infected mouse brain, and Banzi virus, H 336 strain, isolated from the serum of a febrile boy in South Africa, were obtained from ATCC. Vero cells were used with both of these viruses and for assay.

Cells and Media:

MA-104 cells (BioWhittaker, Inc., Walkersville, Md.) and Vero cells (ATCC) were used in Medium 199 with 5% FBS and 0.1% NaHCO$_3$ and without antibiotics. Assay medium for dengue, yellow fever, and Banzi viruses was MEM, 2% FBS, 0.18% NaHCO$_3$ and 50 µg gentamicin/mL.

Antiviral testing of the compounds of the present invention was performed according to the Sidewall and Huffman reference and similar to the above rhinovirus antiviral testing. Adequate cytopathic effect (CPE) readings were achieved after 5-6 days for each of these viruses.

c. Determination of In Vitro Antiviral Activity of Compounds Against West Nile Virus (CPE Inhibition Assay)

Assay details are provided in the Sidewall and Huffman reference cited above. West Nile virus, New York isolate derived from crow brain, was obtained from the Center for Disease Control. Vero cells were grown and used as described above. Test medium was MEM, 1% FBS, 0.1% NaHCO$_3$ and 50 µg gentamnicin/mL.

Antiviral testing of the compounds of the present invention was performed following the methods of Sidewall and Huffman which are similar to those used to assay for rhinovirus activity. Adequate cytopathic effect (CPE) readings were achieved after 5-6 days.

d. Determination of In Vitro Antiviral Activity of Compounds Against Rhino, Yellow Fever, Dengue, Banzi, and West Nile Viruses (Neutral Red Uptake Assay)

After performing the CPE inhibition assays above, an additional cytopathic detection method was used which is described in "Microtiter Assay for Interferon: Microspectrophotometric Quantitation of Cytopathic Effect," *Appl. Environ. Microbiol.* 31: 35-38 (1976). A Model EL309 microplate reader (Bio-Tek Instruments Inc.) was used to read the assay plate. ED50's and CD50's were calculated as above.

EXAMPLE OF A PHARMACEUTICAL FORMULATION

As a specific embodiment of an oral composition of a compound of the present invention, 50 mg of the compound of Example 1 or Example 2 is formulated with sufficient finely divided lactose to provide a total amount of 580 to 590 mg to fill a size O hard gelatin capsule.

While the invention has been described and illustrated in reference to specific embodiments thereof, those skilled in the art will appreciate that various changes, modifications, and substitutions can be made therein without departing from the spirit and scope of the invention. For example, effective dosages other than the preferred doses as set forth heeinabove may be applicable as a consequence of variations in the responsiveness of the human being treated for severity of the HCV infection. Likewise, the pharmacologic response observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended therefore that the invention be limited only by the scope of the claims which follow, and that such claims be interpreted as broadly as is reasonable.

What is claimed is:
1. A compound of the structural formula I:

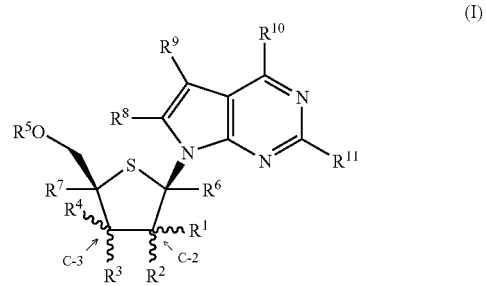

or a pharmaceutically acceptable salt thereof;
wherein R$^1$ is C$_{1-4}$ alkyl, wherein alkyl is unsubstituted or substituted with hydroxy, amino, C$_{1-4}$ alkoxy, C$_{1-4}$ alkylthio, or one to three fluorine atoms;

R$^2$ is amino, fluorine, hydroxy, mercapto, C$_{1-4}$ alkoxy, or C$_{1-10}$ alkylcarbonyloxy;

R$^3$ and R$^4$ are each independently selected from the group consisting of hydrogen, cyano, azido, halogen, hydroxy, mercapto, amino, C$_{1-4}$ alkoxy, C$_{1-10}$ alkylcarbonyloxy, C$_{2-4}$ alkenyl, C$_{2-4}$ alkynyl, and C$_{1-4}$ alkyl, wherein alkyl is unsubstituted or substituted with hydroxy, amino, C$_{1-4}$ alkoxy, C$_{1-4}$ alkylthio, or one to three fluorine atoms;

R$^5$ is hydrogen, C$_{1-10}$ alkylcarbonyl, P$_3$O$_9$H$_4$, P$_2$O$_6$H$_3$, or P(O)R$^{13}$R$^{14}$;

R$^6$ and R$^7$ are each independently hydrogen, methyl, hydroxymethyl, or fluoromethyl;

R$^8$ is hydrogen, C$_{1-4}$ alkyl, C$_{2-4}$ alkynyl, halogen, cyano, carboxy, C$_{1-4}$ alkyloxycarbonyl, azido, amino, C$_{1-4}$ alkylamino, di(C$_{1-4}$ alkyl)amino, hydroxy, C$_{1-6}$ alkoxy, C$_{1-6}$ alkylthio, C$_{1-6}$ alkylsulfonyl, or (C$_{1-4}$ alkyl)$_{0-2}$ aminomethyl;

R$^9$ is hydrogen, nitro, C$_{1-3}$ alkyl, NHCONH$_2$, CONR$^{12}$R$^{12}$, CSNR$^{12}$R$^{12}$, COOR$^{12}$, C(=NH)NH$_2$, hydroxy, C$_{1-3}$ alkoxy, amino, C$_{1-4}$ alkylamino, di(C$_{1-4}$ alkyl)amino, halogen, (1,3-oxazol-2-yl), (1,3-thiazol-2-yl), or (imidazol-2-yl); wherein alkyl is unsubstituted or substituted with one to three groups independently selected from halogen, amino, hydroxy, carboxy, and C$_{1-3}$ alkoxy;

R$^{10}$ and R$^{11}$ are each independently hydrogen, hydroxy, halogen, C$_{1-4}$ alkoxy, amino, C$_{1-4}$ alkylamino, di(C$_{1-4}$ alkyl)amino, C$_{3-6}$ cycloalkylamino, di(C$_{3-6}$ cycloalkyl) amino, or C$_{4-6}$ cycloheteroalkyl, unsubstituted or substituted with one to two groups independently selected from halogen, hydroxy, amino, C$_{1-4}$ alkyl, and C$_{1-4}$ alkoxy;

each R$^{12}$ is independently hydrogen or C$^{1-6}$ alkyl; and

R$^{13}$ and R$^{14}$ are each independently hydroxy, OCH$_2$CH$_2$SC(=O)C$_{1-4}$ alkyl, OCH$_2$O(C=O)OC$_{1-4}$ alkyl, NHCHMeCO$_2$Me, OCH(C$_{1-4}$ alkyl)O(C=O) C$_{1-4}$ alkyl,

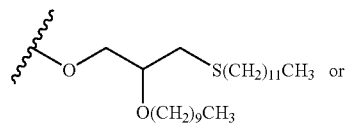

-continued

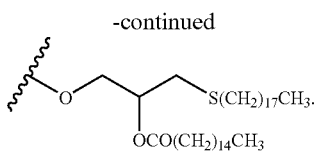

2. The compound of claim 1 of the structural formula II:

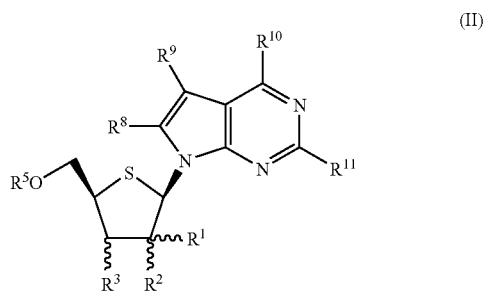

(II)

or a pharmaceutically acceptable salt thereof;
wherein
 $R^1$ is $C_{1-3}$ alkyl, wherein alkyl is unsubstituted or substituted with hydroxy, amino, $C_{1-3}$ alkoxy, $C_{1-3}$ alkylthio, or one to three fluorine atoms;
 $R^2$ is hydroxy, fluoro, $C_{1-3}$ alkoxy, or $C_{1-8}$ alkylcarbonyloxy;
 $R^3$ is hydrogen, halogen, hydroxy, amino, $C_{1-3}$ alkoxy, or $C_{1-8}$ alkylcarbonyloxy;
 $R^5$ is hydrogen, $C_{1-8}$ alkylcarbonyl, $P_3O_9H_4$, $P_2O_6H_3$, or $PO_3H_2$;
 $R^8$ is hydrogen, amino, or $C_{1-4}$ alkylamino;
 $R^9$ is hydrogen, methyl, halogen, or $CONH_2$; and
 $R^{10}$ and $R^{11}$ are each independently hydrogen, halogen, hydroxy, amino, $C_{1-4}$ alkylamino, di($C_{1-4}$ alkyl)amino, or $C_{3-6}$ cycloalkylamino.

3. The compound of claim 2, or a pharmaceutically acceptable salt thereof, wherein
 $R^1$ is methyl, fluoromethyl, hydroxymethyl, difluoromethyl, trifluoromethyl, or aminomethyl;
 $R^2$ is hydroxy, fluoro, or methoxy;
 $R^3$ is hydrogen, fluoro, hydroxy, amino, or methoxy;
 $R^5$ is hydrogen or $P_3O_9H_4$;
 $R^8$ is hydrogen or amino;
 $R^9$ is hydrogen, methyl, halogen, or $CONH_2$; and
 $R^{10}$ and $R^{11}$ are each independently hydrogen, fluoro, hydroxy, or amino.

4. The compound of claim 3 which is selected from the group consisting of:
 4-amino-7-(2-C-methyl-4-thio-β-D-ribofuranosyl)-7H-pyrrolo[2,3-d]pyrimidine;
 2-amino-7-(2-C-methyl-4-thio-β-D-ribofuranosyl)-7H-pyrrolo[2,3-d]pyrimidin-4(3H)-one;
 the corresponding 5'-triphosphates; and
 pharmaceutically acceptable salts thereof.

5. A pharmaceutical composition comprising a compound of claim 1, or a pharmaceutically acceptable salt thereof, and a pharmaceutically acceptable carrier.

6. The pharmaceutical composition of claim 5 useful for inhibiting RNA-dependent RNA viral polymerase, inhibiting RNA-dependent RNA replication, and/or treating RNA-dependent RNA viral infection.

7. The pharmaceutical composition of claim 6 wherein said RNA-dependent RNA viral polymerase is HCV NS5B polymerase, said RNA-dependent RNA viral replication is HCV replication, and said RNA-dependent RNA viral infection is HCV infection.

8. A method of inhibiting HCV NS5B RNA-dependent RNA viral polymerase and/or inhibiting HCV viral replication comprising administering to a mammal in need of such inhibition an effective amount of a compound according to claim 1 or a pharmaceutically acceptable salt thereof.

9. A method of treating HCV infection comprising administering to a mammal in need of such treatment an effective amount of a compound according to claim 1 or a pharmaceutically acceptable salt thereof.

10. The method of claim 9 in combination with a therapeutically effective amount of another agent active against HCV.

11. The method of claim 10 wherein said agent active against HCV is ribavirin; levovirin; thymosin alpha-1; interferon-β; an inhibitor of NS3 serine protease; an inhibitor of inosine monophosphate dehydrogenase; interferon-α or pegylated interferon-α, alone or in combination with ribavirin or levovirin.

12. The method of claim 11 wherein said agent active against HCV is interferon-α or pegylated interferon-α, alone or in combination with ribavirin.

13. A method of treating HCV infection which comprises administering to a mammal in need of such treatment an effective amount of a compound of structural formula II:

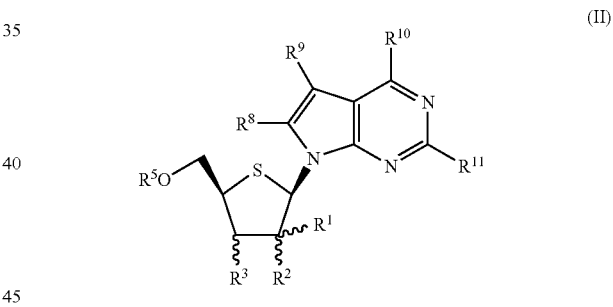

(II)

or a pharmaceutically acceptable salt thereof;
wherein
 $R^1$ is $C_{1-3}$ alkyl, wherein alkyl is unsubstituted or substituted with hydroxy, amino, $C_{1-3}$ alkoxy, $C_{1-3}$ alkylthio, or one to three fluorine atoms;
 $R^2$ is hydroxy, fluoro, $C_{1-3}$ alkoxy, or $C_{1-8}$ alkylcarbonyloxy;
 $R^3$ is hydrogen, halogen, hydroxy, amino, $C_{1-3}$ alkoxy, or $C_{1-8}$ alkylcarbonyloxy;
 $R^5$ is hydrogen, $C_{1-8}$ alkylcarbonyl, $P_3O_9H_4$, $P_2O_6H_3$, or $PO_3H_2$;
 $R^8$ is hydrogen, amino, or $C_{1-4}$ alkylamino;
 $R^9$ is hydrogen, cyano, methyl, halogen, or $CONH_2$; and
 $R^{10}$ and $R^{11}$ are each independently hydrogen, halogen, hydroxy, amino, $C_{1-4}$ alkylamino, di($C_{1-4}$ alkyl)amino, or $C_{3-6}$ cycloalkylamino.

14. The method according to claim 13, wherein in the compound of formula II, or a pharmaceutically acceptable salt thereof:

$R^1$ is methyl, fluoromethyl, hydroxymethyl, difluoromethyl, trifluoromethyl, or aminomethyl;

$R^2$ is hydroxy, fluoro, or methoxy;

$R^3$ is hydrogen, fluoro, hydroxy, amino, or methoxy;

$R^5$ is hydrogen or $P_3O_9H_4$;

$R^8$ is hydrogen or amino;

$R^9$ is hydrogen, cyano, methyl, halogen, or $CONH_2$; and $R^{10}$ and $R^{11}$ are each independently hydrogen, fluoro, hydroxy, or amino.

15. The method according to claim 14, wherein the compound is selected from the group consisting of:

4-amino-7-(2-C-methyl-4-thio-β-D-ribofuranosyl)-7H-pyrrolo[2,3-d]pyrimidine;

2-amino-7-(2-C-methyl-4-thio-β-D-ribofuranosyl)-7H-pyrrolo[2,3-d]pyrimidin-4(3H)-one; corresponding 5'-triphosphates; and pharmaceutically acceptable salts thereof.

* * * * *